United States Patent
Matsuda et al.

(10) Patent No.: US 10,444,181 B2
(45) Date of Patent: Oct. 15, 2019

(54) SULFUR OXIDE DETECTION SYSTEM

(71) Applicant: TOYOTA JIDOSHA KABUSHIKI KAISHA, Aichi-ken (JP)

(72) Inventors: Kazuhisa Matsuda, Susono (JP); Kazuhiro Wakao, Susono (JP); Keiichiro Aoki, Shizuoka-ken (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 339 days.

(21) Appl. No.: 15/438,750

(22) Filed: Feb. 21, 2017

(65) Prior Publication Data

US 2017/0248539 A1 Aug. 31, 2017

(30) Foreign Application Priority Data

Feb. 29, 2016 (JP) ................................. 2016-037480

(51) Int. Cl.
*G01N 27/407* (2006.01)
*G01N 27/406* (2006.01)
*G01N 27/30* (2006.01)
*G01N 27/416* (2006.01)
*G01N 33/00* (2006.01)
*F02D 19/06* (2006.01)
*G01N 27/419* (2006.01)

(52) U.S. Cl.
CPC ..... *G01N 27/4065* (2013.01); *F02D 19/0657* (2013.01); *G01N 27/304* (2013.01); *G01N 27/4071* (2013.01); *G01N 27/4074* (2013.01); *G01N 27/4077* (2013.01); *G01N 27/419* (2013.01); *G01N 27/4163* (2013.01); *G01N 33/0042* (2013.01); *F01N 2560/027* (2013.01); *F02D 2200/0818* (2013.01); *Y02A 50/248* (2018.01); *Y02T 10/36* (2013.01)

(58) Field of Classification Search
CPC ...... G01N 27/407–41; F01N 2560/027; F01N 2560/026; F02D 35/0015
See application file for complete search history.

(56) References Cited

U.S. PATENT DOCUMENTS 6,007,697 A * 12/1999 Yagi ................... G01N 27/4175
204/402
9,753,005 B2 * 9/2017 Kato .................. G01N 27/4074
2001/0023823 A1 * 9/2001 Takahashi ............ G01N 27/419
204/426

FOREIGN PATENT DOCUMENTS

JP 11-190721 A 7/1999
WO WO 2014112315 * 7/2014 ............. G01N 27/41

* cited by examiner

*Primary Examiner* — Alexander S Noguerola
(74) *Attorney, Agent, or Firm* — Hauptman Ham, LLP

(57) ABSTRACT

A sulfur oxide detection system includes an element part which includes a sensor cell and a diffusion regulating layer. The sensor cell includes a solid electrolyte layer, a first electrode arranged, and a second electrode. The sulfur oxide detection system also includes a voltage application circuit configured to apply a voltage to the sensor cell so that a potential of the second electrode becomes higher than a potential of the first electrode, and a current detection circuit configured to detect a current flowing between the first electrode and the second electrode. The sulfur oxide detection system further includes a controller coupled with the voltage application circuit and the current detection circuit, and configured to estimate a sulfur oxide concentration in a gas to which the first electrode is exposed by way of the diffusion layer.

15 Claims, 16 Drawing Sheets

SULFUR OXIDE DETECTION SYSTEM

CROSS-REFERENCE TO RELATED APPLICATION

This application claims priority under 35 USC 119 from Japanese Patent Application No. 2016-037480 filed on Feb. 29, 2016, the disclosure of which is incorporated by reference herein.

BACKGROUND

Fuel used in an internal combustion engine, in particular fossil fuel, contains trace amounts of sulfur (S) ingredients. The sulfur ingredients contained in fuel in this way invite deterioration of component parts in an exhaust system of an internal combustion engine etc. Further, if frequently performing control suppressing deterioration of the component parts due to the sulfur ingredients or control for regenerating deteriorated component parts, deterioration of the fuel efficiency is invited. Therefore, in order to keep the deterioration of the fuel efficiency etc. at a minimum extent while keeping the deterioration of the component parts at a minimum extent, it is desirable to detect the content of sulfur ingredients in the fuel.

If the fuel used in an internal combustion engine contains sulfur ingredients, the exhaust gas discharged from a combustion chamber contains sulfur oxide ($SO_X$). Further, the higher the content of the sulfur ingredients in the fuel, the higher the concentration of $SO_X$ in the exhaust gas. Therefore, if it is possible to detect the concentration of $SO_X$ in exhaust gas, it is possible to estimate the content of sulfur ingredients in the fuel.

SUMMARY

An aspect of this description is direct to a sulfur oxide detection system comprising an element part which includes a sensor cell having a solid electrolyte layer having oxide ion conductivity, a first electrode arranged on one side surface of the solid electrolyte layer so as to be exposed to a measured gas, and a second electrode arranged at the other side surface of the solid electrolyte layer to be exposed to an atmosphere and includes a diffusion regulating layer regulating diffusion of the measured gas and which is arranged in an exhaust passage of an internal combustion engine. The sulfur oxide detection system also comprises a voltage application circuit configured to apply a voltage to the sensor cell so that a potential of the second electrode becomes higher than a potential of the first electrode. The sulfur oxide detection system further comprises a current detection circuit configured to detect a current flowing between the first electrode and the second electrode. The sulfur oxide detection system additionally comprises a controller communicatively coupled with the voltage application circuit and the current detection circuit. The controller is configured to perform first control making the voltage applied to the sensor cell rise from a first voltage less than a decomposition start voltage of water and sulfur oxide to a second voltage higher than the decomposition start voltage so that a voltage of the decomposition start voltage or more is applied to the sensor cell for a first period of time, after the first control, perform second control making the voltage applied to the sensor cell rise from the first voltage to the second voltage so that the voltage of the decomposition start voltage or more is applied to the sensor cell for a second period of time different from the first period of time, and, between the first control and the second control, perform poisoning recovery control applying a voltage enabling desorption of decomposition products of sulfur oxide adsorbed at the first electrode to the sensor cell. The controller is also configured to estimate a sulfur oxide concentration in the measured gas based on a difference or a ratio of a first current detected by the current detection circuit when the first control is performed and a second current detected by the current detection circuit when the second control is performed.

In a second aspect, the controller is configured to make the voltage applied to the sensor cell rise from the first voltage to the second voltage by a voltage waveform of a sine wave having a first period of 0.1 second to 100 seconds in the first control, and make the voltage applied to the sensor cell rise from the first voltage to the second voltage by a voltage waveform of a sine wave having a second period of 0.1 second to 100 seconds different from the first period in the second control, in the first aspect.

In a third aspect, the controller is configured to make the voltage applied to the sensor cell rise from the first voltage to the second voltage by a voltage waveform of a square wave having a first time constant of 0.05 second to 50 seconds in the first control, and make the voltage applied to the sensor cell rise from the first voltage to the second voltage by a voltage waveform of a square wave having a second time constant of 0.05 second to 50 seconds different from the first time constant in the second control, in the first aspect.

In a fourth aspect, the controller is configured to estimate the sulfur oxide concentration in the measured gas based on the difference of the first current and the second current, and estimate that the sulfur oxide concentration in the measured gas is a reference concentration or more when the difference is a reference value or more, in any one of the first to third aspects.

In a fifth aspect, the controller is configured to estimate the sulfur oxide concentration in the measured gas based on the ratio of the first current and the second current, and estimate that the sulfur oxide concentration in the measured gas is a reference concentration or more when the ratio is a reference value or more, and the controller is configured to calculate the ratio by dividing the first current by the second current if the first period of time is shorter than the second period of time and by dividing the second current by the first current if the first period of time is longer than the second period of time, in any one of the first to third aspects.

In a sixth aspect, the controller is configured to estimate the sulfur oxide concentration in the measured gas based on the ratio of the first current and the second current, and estimate that the sulfur oxide concentration in the measured gas is a reference concentration or more if the ratio is a reference value or less, and the controller is configured to calculate the ratio by dividing the second current by the first current if the first period of time is shorter than the second period of time and by dividing the first current by the second current if the first period of time is longer than the second period of time, in any one of the first to third aspects.

In a seventh aspect, the first period of time is shorter than the second period of time, in any one of the first to sixth aspects.

In an eighth aspect, the controller is configured to estimate that the sulfur oxide concentration in the measured gas is an upper limit concentration or more if the first current is a lower limit value or less, in any one of the first to seventh aspects.

In a ninth aspect, the controller is configured to estimate that the sulfur oxide concentration in the measured gas is an upper limit concentration or more if the first current is a first lower limit value or less and the second current is a second lower limit value or less, in any one of the first to seventh aspects.

In a tenth aspect, the controller is configured to judge whether an air-fuel ratio of the measured gas and a temperature of the element part are stable, and the controller is configured to perform the first control, the poisoning recovery control, and the second control while it is judged that the air-fuel ratio of the measured gas and the temperature of the element part are stable, in any one of the first to ninth aspects.

In an eleventh aspect, the first current is a maximum value of current detected by the current detection circuit when the first control is performed and the second current is a maximum value of current detected by the current detection circuit when the second control is performed, in any one of the first to tenth aspects.

In a twelfth aspect, if the difference or the ratio of the first current and the second current is less than a predetermined value, the controller is configured to perform third control making the voltage applied to the sensor cell rise from the first voltage to the second voltage after the second control so that the voltage of the decomposition start voltage or more is applied to the sensor cell for a third period of time, perform fourth control making the voltage applied to the sensor cell rise from the first voltage to the second voltage after the third control so that the voltage of the decomposition start voltage or more is applied to the sensor cell for a fourth period of time, and perform the poisoning recovery control between the second control and the third control and between the third control and the fourth control, the controller is configured to calculate the ratio by dividing the first current by the second current if the first period of time is shorter than the second period of time and by dividing the second current by the first current if the first period of time is longer than the second period of time, a sum of the first period of time and the second period of time is smaller than a sum of the third period of time and the fourth period of time and a difference of the third period of time and the fourth period of time is larger than a difference of the first period of time and the second period of time, and the controller is configured to estimate the sulfur oxide concentration in the measured gas based on a difference or a ratio of the third current detected by the current detection circuit when the third control is performed and the fourth current detected by the current detection circuit when the fourth control is performed, in any one of the first to eleventh aspects.

In a thirteenth aspect, if the ratio of the first current and the second current is higher than a predetermined value, the controller is configured to perform third control making the voltage applied to the sensor cell rise from the first voltage to the second voltage after the second control so that the voltage of the decomposition start voltage or more is applied to the sensor cell for a third period of time, perform fourth control making the voltage applied to the sensor cell rise from the first voltage to the second voltage after the third control so that the voltage of the decomposition start voltage or more is applied to the sensor cell for a fourth period of time, and perform the poisoning recovery control between the second control and the third control and between the third control and the fourth control, the controller is configured to calculate the ratio by dividing the second current by the first current if the first period of time is shorter than the second period of time and by dividing the first current by the second current if the first period of time is longer than the second period of time, a sum of the first period of time and the second period of time is smaller than a sum of the third period of time and the fourth period of time and a difference of the third period of time and the fourth period of time is larger than a difference of the first period of time and the second period of time, and the controller is configured to estimate the sulfur oxide concentration in the measured gas based on a difference or a ratio of the third current detected by the current detection circuit when the third control is performed and the fourth current detected by the current detection circuit when the fourth control is performed, in any one of the first to eleventh aspects.

In a fourteenth aspect, the third period of time is shorter than the fourth period of time, in the twelfth or thirteenth aspect.

BRIEF DESCRIPTION OF DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
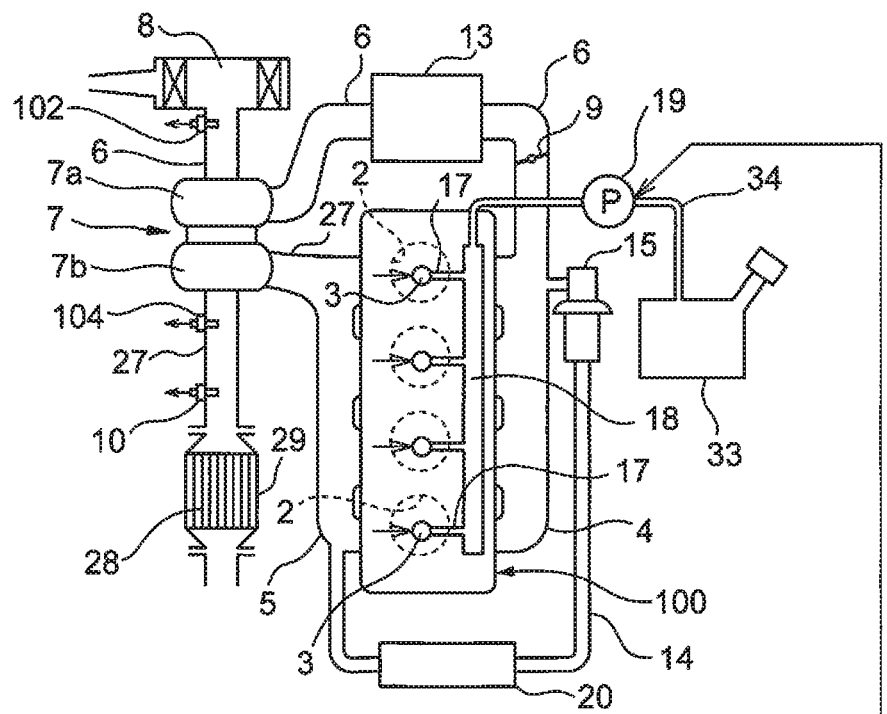
FIG. 1 is a view schematically showing an internal combustion engine in which an $SO_X$ detection system according to a first embodiment of the present invention is used.

Below, referring to the drawings, embodiments of the present invention will be explained in detail. Note that, in the following description, similar component elements will be assigned the same reference notations.

First, referring to FIG. 1 to FIG. 12, a first embodiment of the present invention will be explained.

FIG. 1 is a view schematically showing an internal combustion engine in which a sulfur oxide detection system according to the first embodiment of the present invention (below, referred to as "$SO_X$ detection system") is used. The internal combustion engine shown in FIG. 1 is a compression self-ignition type internal combustion engine (diesel engine). The internal combustion engine is, for example, carried in a vehicle.

Referring to FIG. 1, the internal combustion engine comprises an engine body 100, a combustion chamber 2 of each cylinder, an electronic control type fuel injector 3 injecting fuel into each combustion chamber 2, an intake manifold 4, and an exhaust manifold 5. The intake manifold 4 is connected through an intake pipe 6 to an outlet of a compressor 7a of a turbocharger 7. An inlet of the compressor 7a is connected through the intake pipe 6 to an air cleaner 8. Inside the intake pipe 6, a throttle valve 9 driven by a step motor is arranged. Furthermore, around the intake pipe 6, a cooling device 13 is arranged for cooling the intake air flowing through the inside of the intake pipe 6. In the internal combustion engine shown in FIG. 1, engine cooling water is guided to the inside of the cooling device 13 where the engine cooling water is used to cool the intake air. The intake manifold 4 and intake pipe 6 form an intake passage for guiding air to the combustion chamber 2.

On the other hand, the exhaust manifold 5 is connected through an exhaust pipe 27 to an inlet of a turbine 7b of the turbocharger 7. An outlet of the turbine 7b is connected through the exhaust pipe 27 to a casing 29 housing an exhaust purification catalyst 28. The exhaust manifold 5 and exhaust pipe 27 form an exhaust passage for discharging exhaust gas generated by combustion of the air-fuel mixture in the combustion chamber 2. The exhaust purification catalyst 28 is, for example, a selective reduction type $NO_X$ reduction catalyst removing $NO_X$ in exhaust gas by reduction (SCR catalyst) or an $NO_X$ storage reduction catalyst. Further, in the exhaust passage, to reduce the particulate matter (PM) in the exhaust gas, an oxidation catalyst, diesel particulate filter (DPF), etc. may be arranged.

The exhaust manifold 5 and the intake manifold 4 are connected with each other through an exhaust gas recirculation (below, "EGR") passage 14. Inside the EGR passage 14, an electronic control type EGR control valve 15 is arranged. Further, around the EGR passage 14, an EGR cooling device 20 is arranged for cooling the EGR gas flowing through the inside of the EGR passage 14. In the embodiment shown in FIG. 1, engine cooling water is guided to the inside of the EGR cooling device 20 where the engine cooling water is used to cool the EGR gas.

The fuel is supplied by an electronic control type variable discharge fuel pump 19 from a fuel tank 33 through a fuel pipe 34 to the inside of a common rail 18. The fuel supplied to the inside of the common rail 18 is supplied through each fuel feed tube 17 to fuel injectors 3.

The various control routines of the internal combustion engine are performed by an electronic control unit (ECU) 80. The ECU 80 is a digital computer having components connected with each other by a bidirectional bus 81 such as a ROM (read only memory) 82, RAM (random access memory) 83, CPU (microprocessor) 84, input port 85, and output port 86. The outputs of a load sensor 101, air flow meter 102 and air-fuel ratio sensor 104 are input through corresponding AD converters 87 to the input port 85. On the other hand, the output port 86 is connected through corresponding drive circuits 88 to the fuel injectors 3, throttle valve drive step motor, EGR control valve 15, and fuel pump 19.

The load sensor 101 generates an output voltage proportional to an amount of depression of an accelerator pedal 120. Therefore, the load sensor 101 detects an engine load. The air flow meter 102 is arranged in the intake passage between the air cleaner 8 and the compressor 7a and detects the air flow rate flowing through the inside of the intake pipe 6. The air-fuel ratio sensor 104 is arranged in the exhaust passage between the turbine 7b and the exhaust purification catalyst 28 and detects the exhaust air-fuel ratio of the exhaust gas. Furthermore, a crank angle sensor 108 generating an output pulse each time a crankshaft rotates by for example 15° is connected to the input port 85. The crank angle sensor 108 detects the engine speed.

Note that, the internal combustion engine in which the internal $SO_X$ detection system is used may also be a spark ignition type internal combustion engine in which spark plugs are arranged at the combustion chambers. Further, the specific configuration of the internal combustion engine such as an arrangement of the cylinders, configuration of the intake and exhaust systems, and the provision of a supercharger may differ from the configuration shown in FIG. 1.

Below, referring to FIG. 1 to FIG. 3, an $SO_X$ detection system 1 according to the first embodiment of the present invention will be explained. The $SO_X$ detection system 1 detects the sulfur oxide ($SO_X$) concentration in the exhaust gas flowing through the inside of the exhaust passage of the internal combustion engine.

Figure 2:
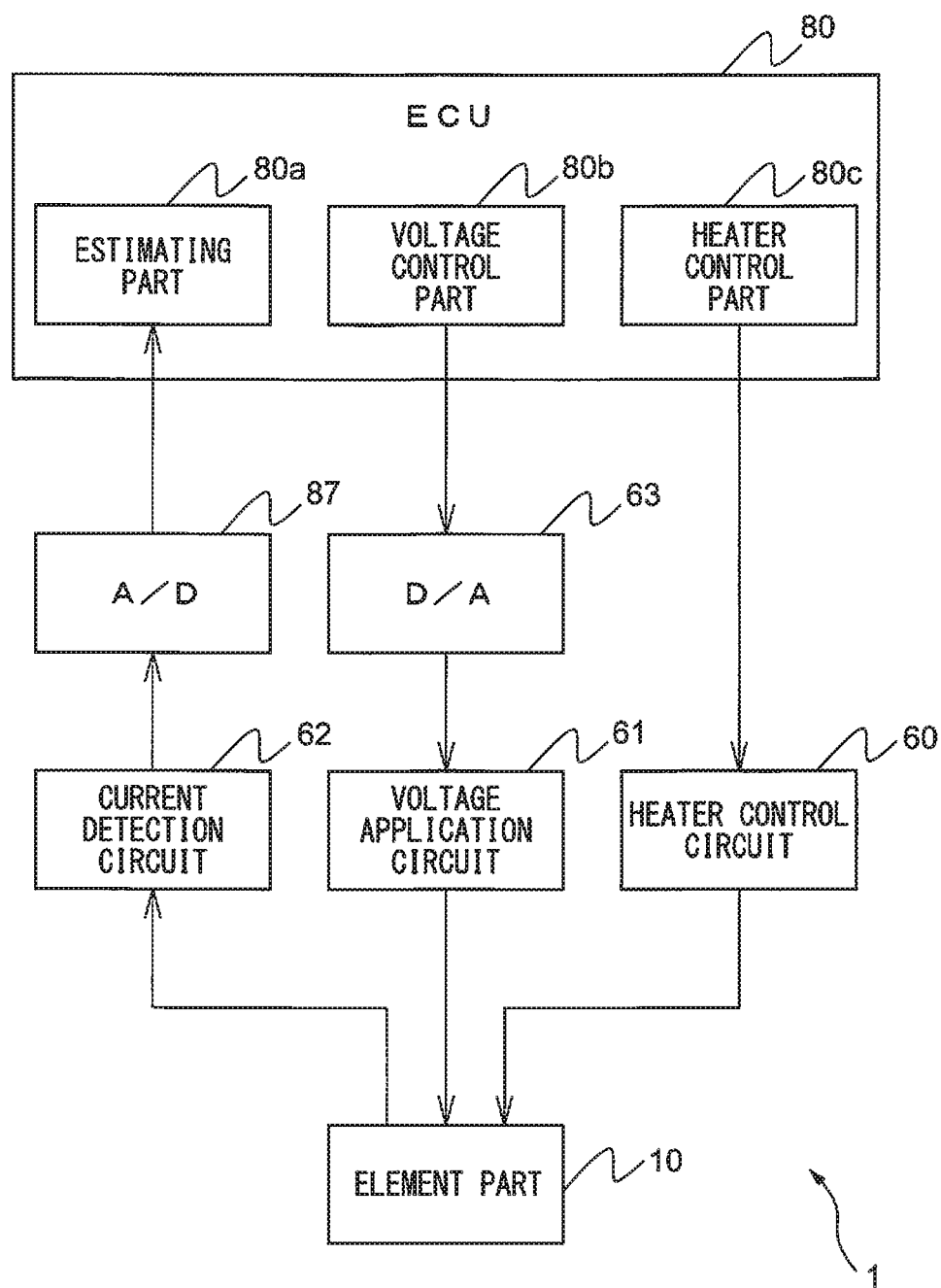
FIG. 2 is a schematic block diagram showing the configuration of the $SO_X$ detection system according to the first embodiment of the present invention.

FIG. 2 is a schematic block diagram showing the configuration of the $SO_X$ detection system 1 according to the first embodiment of the present invention. As shown in FIG. 2, the $SO_X$ detection system 1 comprises an element part 10, a heater control circuit 60, a voltage application circuit 61, and a current detection circuit 62 which are connected to the element part 10, and the ECU 80. The ECU 80 includes an estimating part 80a, voltage control part 80b, and heater control part 80c. Further, the $SO_X$ detection system 1 further comprises a DA converter 63 connected to the voltage control part 80b of the ECU 80 and a voltage application circuit 62, and an AD converter 87 connected to the estimating part 80a of the ECU 80 and current detection circuit 62.

As shown in FIG. 1, the element part 10 is arranged in the exhaust passage of the internal combustion engine between the turbine 7b and the exhaust purification catalyst 28. In other words, the element part 10 is arranged in the exhaust passage at the upstream side of the exhaust purification catalyst 28 in the direction of exhaust flow. Note that, the element part 10 may be arranged at another position of the exhaust passage, for example, the downstream side of the exhaust purification catalyst 28 in the direction of exhaust flow.

Figure 3:
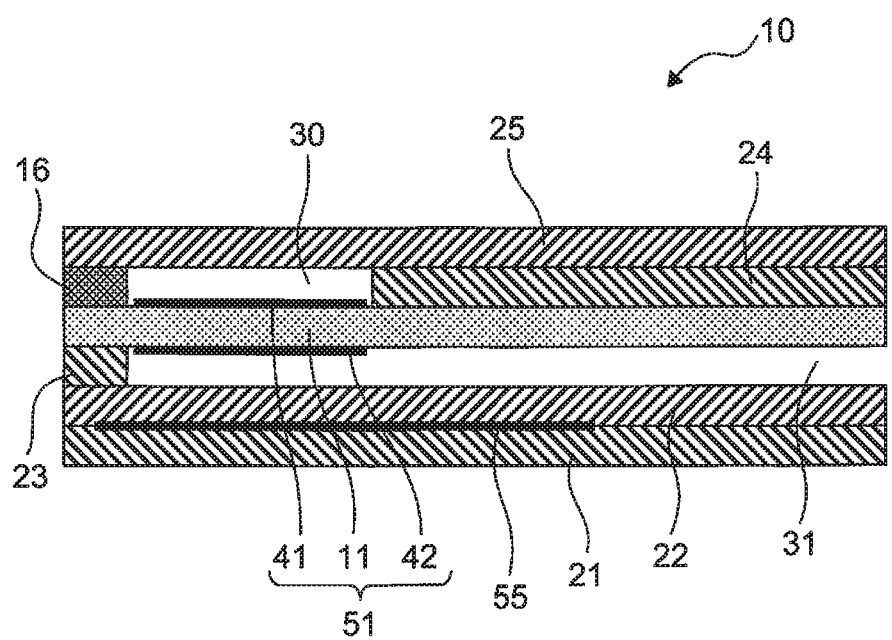
FIG. 3 is a schematic cross-sectional view showing the configuration of an element part of the $SO_X$ detection system according to the first embodiment of the present invention.

FIG. 3 is a schematic cross-sectional view showing the configuration of the element part 10 of the $SO_X$ detection system 1. As shown in FIG. 3, the element part 10 comprises a plurality of layers laminated together. Specifically, the element part 10 comprises a first solid electrolyte layer 11, a diffusion regulating layer 16, a first barrier layer 21, a second barrier layer 22, a third barrier layer 23, a fourth barrier layer 24, and a fifth barrier layer 25.

The first solid electrolyte layer 11 is a thin sheet member having oxide ion conductivity. The first solid electrolyte layer 11 is, for example, formed by a sintered member of $ZrO_2$ (zirconia), $HfO_2$, $ThO_2$, $Bi_2O_3$, to which CaO, MgO, $Y_2O_3$, $Yb_2O_3$, etc. is added as a stabilizer. Further, the diffusion regulating layer 16 is a thin sheet member having gas permeability. The diffusion regulating layer 16 is, for example, formed by a porous sintered body of alumina, magnesia, silica, spinel, mullite, or other heat resistant inorganic substance. The barrier layers 21 to 25 are thin sheet members having gas barrier property and are formed, for example, as layers containing alumina.

The layers of the element part 10 are stacked, from the bottom of FIG. 3, in the order of the first barrier layer 21, second barrier layer 22, third barrier layer 23, first solid electrolyte layer 11, diffusion regulating layer 16 and fourth barrier layer 24, and fifth barrier layer 25. The first solid electrolyte layer 11, diffusion regulating layer 16, fourth barrier layer 24, and fifth barrier layer 25 are used to define and form a measured gas chamber 30. The measured gas chamber 30 is configured so that when the element part 10 is arranged in the exhaust passage, the exhaust gas of the internal combustion engine (measured gas) flows into the measured gas chamber 30 through the diffusion regulating layer 16. That is, the element part 10 is arranged in the exhaust passage so that the diffusion regulating layer 16 is exposed to the exhaust gas. Therefore, the measured gas chamber 30 communicates with the exhaust passage through the diffusion regulating layer 16. Note that, the measured gas chamber 30 may be configured in any way so long as it adjoins the first solid electrolyte layer 11 and is configured so that the measured gas flows into it.

Further, the first solid electrolyte layer 11, second barrier layer 22, and third barrier layer 23 are used to define and form a first atmospheric chamber 31. As will be understood from FIG. 3, the first atmospheric chamber 31 is arranged across the first solid electrolyte layer 11 at a side opposite to the measured gas chamber 30. The first atmospheric chamber 31 is open to the atmospheric air outside the exhaust passage. Therefore, atmospheric air flows into the first atmospheric chamber 31. Note that, the first atmospheric chamber 31 may be configured in any way so long as it adjoins the first solid electrolyte layer 11 and is configured so that atmospheric air flows into it.

The element part 10 further comprises a first electrode 41 and a second electrode 42. The first electrode 41 is arranged on the surface of the first solid electrolyte layer 11 at the measured gas chamber 30 side. Therefore, the first electrode 41 is exposed to the measured gas in the measured gas chamber 30. On the other hand, the second electrode 42 is arranged on the surface of the first solid electrolyte layer 11 at the first atmospheric chamber 31 side. Therefore, the second electrode 42 is exposed to the gas inside the first atmospheric chamber 31 (atmospheric air). The first electrode 41 and the second electrode 42 are arranged facing each other across the first solid electrolyte layer 11. The first electrode 41, first solid electrolyte layer 11, and second electrode 42 form the first electrochemical cell 51. The first electrochemical cell 51 functions as a sensor cell decomposing water and $SO_X$ in the measured gas.

In the present embodiment, the material forming the first electrode 41 includes platinum (Pt), rhodium (Rh), palladium (Pd), and other platinum group elements or alloys of the same as main ingredients. Preferably, the first electrode 41 is a porous cermet electrode containing at least one of platinum (Pt), rhodium (Rh), and palladium (Pd) as main ingredients. However, the material forming the first electrode 41 is not necessarily limited to the above materials. It may be any material so long as when a predetermined voltage is applied between the first electrode 41 and the second electrode 42, it can decompose by reduction the water and $SO_X$ contained in the measured gas inside the measured gas chamber 30.

Further, in the present embodiment, the second electrode 42 is a porous cermet electrode containing platinum (Pt) as a main ingredient. However, the material forming the second electrode 42 is not necessarily limited to the above material and may be any material which, when a predetermined voltage is applied between the first electrode 41 and the second electrode 42, can make oxide ions move between the first electrode 41 and the second electrode 42.

The element part 10 further comprises a heater (electric heater) 55. In the present embodiment, the heater 55, as shown in FIG. 3, is arranged between the first barrier layer 21 and the second barrier layer 22. The heater 55 is, for example, a thin sheet member of cermet containing platinum (Pt) and a ceramic (for example, alumina etc.) and is a heat generating member generating heat by application of current. The heater 55 of the element part 10 is connected to the heater control circuit 60. The heater control part 80c of ECU 80 inputs the heater control signal to the heater control circuit 60 and controls the heater 55 via the heater control circuit 60. Due to this, the heater 55 can heat the first electrochemical cell 51 to an activation temperature or more.

The first electrode 41 and the second electrode 42 are connected to the voltage application circuit 61. The voltage application circuit 61 applies voltage to the first electrochemical cell 51 so that the potential of the second electrode 42 becomes higher than the potential of the first electrode 41. The voltage control part 80b of the ECU 80 inputs the voltage control signal through the DA converter 63 to the voltage application circuit 61 and controls the voltage applied from the voltage application circuit 61 to the first electrochemical cell 51.

The current detection circuit 62 detects the inter-electrode current flowing between the first electrode 41 and the second electrode 42 (that is, the current flowing through the inside of the first solid electrolyte layer 11). The output of the current detection circuit 62 is input through the AD converter 87 to the estimating part 80a of the ECU 80. Therefore, the estimating part 80a can acquire the inter-electrode current detected by the current detection circuit 62 from the current detection circuit 62.

The voltage application circuit 61 functions as a voltage applying part for applying voltage to the first electrochemical cell 51. The current detection circuit 62 functions as a current detecting part for detecting an inter-electrode current flowing between the first electrode 41 and the second electrode 42. The ECU 80 functions as a control device for controlling the element part 10.

Next, the principle of detection of $SO_X$ by the $SO_X$ detection system 1 will be explained. In explaining the principle of detection of $SO_X$, first, the limit current characteristic of oxygen in the element part 10 will be explained. At the element part 10, if applying voltage across the electrodes using the first electrode 41 at the measured gas chamber 30 side as the cathode and the second electrode 42 at the first atmospheric chamber 31 side as the anode, the oxygen contained in the measured gas is decomposed by reduction and becomes oxide ions. The oxide ions are conducted through the first solid electrolyte layer 11 of the first electrochemical cell 51 from the cathode side to the anode side where they become oxygen which is discharged into the atmosphere. In this Description, such a movement of oxygen by conduction of oxide ions from the cathode side to anode side through the solid electrolyte layer will be called the "oxygen pumping action".

Due to the conduction of oxide ions accompanying such an oxygen pumping action, an inter-electrode current flows across the first electrode 41 and the second electrode 42 forming the first electrochemical cell 51. This inter-electrode current increases with an increase in the voltage applied between the first electrode 41 and the second electrode 42. This is because the higher the applied voltage, the greater the amount of conduction of oxide ions.

However, if the applied voltage is gradually raised and becomes a certain fixed value or more, the inter-electrode current can no longer become larger and is held at a constant value. Such a characteristic is called the "limit current characteristic of oxygen", while the voltage region where the limit current characteristic of oxygen occurs is called the "limit current region of oxygen". Such a limit current characteristic of oxygen occurs due to the speed of conduction of oxide ions able to be conducted through the inside of the solid electrolyte layer 11 along with application of voltage exceeding the speed of introduction of oxygen introduced into the measured gas chamber 30 through the diffusion regulating layer 16. That is, it occurs due to the decomposition reaction of oxygen by reduction at the cathode being a state regulated in diffusion.

Therefore, the inter-electrode current (limit current) when a voltage in the limit current region is applied to the first electrochemical cell 51 corresponds to the concentration of oxygen in the measured gas. By utilizing such a limit current characteristic of oxygen, it is possible to detect the concentration of oxygen in the measured gas and use the detected concentration as the basis to detect the air-fuel ratio of the exhaust gas.

In this regard, the above-mentioned oxygen pumping action is not an action expressed only in the oxygen contained in the measured gas. In gases containing oxygen atoms in the molecules, there are also gases where the oxygen pumping action can be expressed. As such a gas, $SO_X$ and water ($H_2O$) may be mentioned. Therefore, by applying a voltage of the decomposition start voltage of the $SO_X$ and water or more between the first electrode 41 and the second electrode 42 of the first electrochemical cell 51, the water and $SO_X$ contained in the measured gas are decomposed. The oxide ions generated due to the decomposition of $SO_X$ and water are conducted by the oxygen pumping action from the first electrode 41 to the second electrode 42. For this reason, inter-electrode current flows between the first electrode 41 and the second electrode 42.

However, the concentration of $SO_X$ in the exhaust gas is extremely low. The inter-electrode current which is generated due to decomposition of $SO_X$ is also extremely small. In particular, exhaust gas contains a large amount of water and due to the decomposition of water, inter-electrode current flows. For this reason, it is difficult to precisely detect the inter-electrode current occurring due to decomposition of $SO_X$ separately.

As opposed to this, the inventors of the present application discovered that in an electrochemical cell having an oxygen pumping action, the decomposition current when the water and $SO_X$ are decomposed changes depending on the concentration of $SO_X$ in the exhaust gas. The specific principle why this phenomenon occurs is not necessarily clear, but it is believed that this occurs due to the following mechanism.

As explained above, if applying a predetermined voltage of the decomposition start voltage of $SO_X$ or more across the first electrode 41 and the second electrode 42 of the first electrochemical cell 51, the $SO_X$ contained in the measured gas is decomposed. As a result, the decomposition products of the $SO_X$ (for example, sulfur and sulfur compounds) are adsorbed on the cathode comprised of the first electrode 41. As a result, the area of the first electrode able to contribute to the decomposition of water decreases. If the concentration of $SO_X$ in the measured gas is high, decomposition products adsorbed on the first electrode 41 become more. As a result, the decomposition current of water flowing between the electrodes when applying a predetermined voltage of the decomposition start voltage of water or more across the first electrode 41 and the second electrode 42 becomes relatively small. On the other hand, if the concentration of $SO_X$ in the measured gas is low, decomposition products adsorbed on the first electrode 41 becomes less. As a result, the decomposition current of water flowing between the electrodes when applying a predetermined voltage of the decomposition start voltage of water or more across the first electrode 41 and the second electrode 42 becomes relatively high. Therefore, the decomposition current of water flowing between the electrodes changes in accordance with the concentration of $SO_X$ in the measured gas. Using this phenomenon, it becomes possible to detect the concentration of $SO_X$ in the measured gas.

Here, the decomposition start voltage of water is seen to fluctuate somewhat depending on the measurement conditions etc., but is about 0.6V. Further, the decomposition start voltage of $SO_X$ is the same extent as the decomposition start voltage of water or slightly lower than that. Therefore, in the present embodiment, in order to use the above method to detect the concentration of $SO_X$ in the measured gas by the first electrochemical cell 51, 0.6V or more of voltage is applied across the first electrode 41 and the second electrode 42. Further, if the applied voltage is too high, decomposition of the first solid electrolyte layer 11 may be invited. In this case, it is difficult to precisely detect the concentration of $SO_X$ in the measured gas based on the inter-electrode current. For this reason, in the present embodiment, in order to use the above method to detect the concentration of $SO_X$ in the measured gas, a voltage of 0.6V to less than 2.0V is applied across the first electrode 41 and the second electrode 42.

Figure 4:
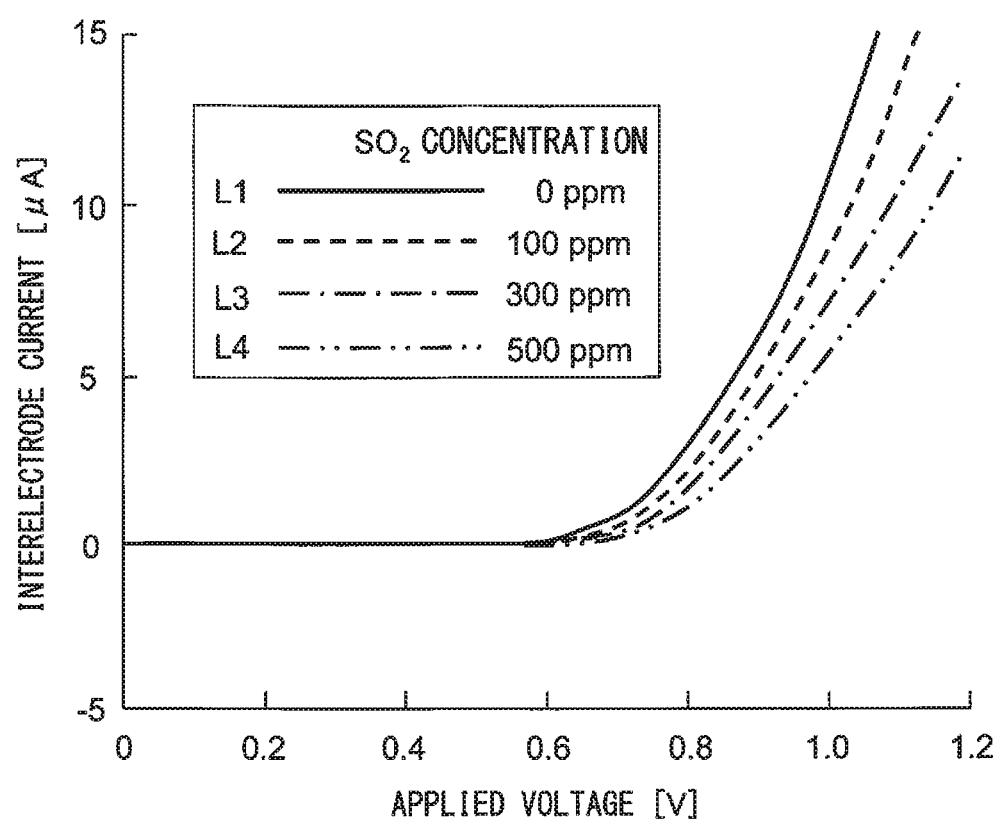
FIG. 4 is a graph showing a relationship between a voltage applied between electrodes of a first electrochemical cell and inter-electrode current flowing between electrodes of the first electrochemical cell.

Below, the relationship between the applied voltage and the inter-electrode current will be specifically explained. FIG. 4 is a schematic graph showing the relationship between the applied voltage and inter-electrode current when gradually raising the applied voltage (pressure raising sweep) in the first electrochemical cell 51. In the illustrated example, four types of measured gas with different concentrations of the $SO_2$ (that is, $SO_X$) contained in the measured gas (0 ppm, 100 ppm, 300 ppm, and 500 ppm) were used. Note that, the concentration of oxygen in the measured gas reaching the first electrode (cathode) 41 of the first electrochemical cell 51 is maintained constant (about 0 ppm) no matter what the measured gas.

The solid line L1 in FIG. 4 shows the relationship between the applied voltage and the inter-electrode current when the $SO_2$ concentration in the measured gas is 0 ppm. In the example shown in FIG. 4, the concentration of oxygen in the measured gas is maintained at substantially 0 ppm, so in the region where the applied voltage is less than about 0.6V, the inter-electrode current is substantially 0. On the other hand, if the applied voltage becomes about 0.6V or more, the inter-electrode current starts to increase along with an increase of the applied voltage. The increase of this inter-electrode current is due to the start of decomposition of water at the first electrode 41.

The broken line L2 in FIG. 4 shows the relationship between the applied voltage and the inter-electrode current in the case where the $SO_2$ concentration in the measured gas is 100 ppm. In this case as well, in the region where the applied voltage is less than about 0.6V, in the same way as the case of the solid line L1, the inter-electrode current is substantially 0. On the other hand, when the applied voltage is about 0.6V or more, inter-electrode current flows due to decomposition of water. However, the inter-electrode current at this time (broken line L2) is smaller compared with the solid line L1. Further, the rate of increase of the inter-electrode current with respect to the applied voltage (slope of broken line L2) also is smaller compared with the solid line L1.

The one-dot chain line L3 in FIG. 4 shows the relationship between the applied voltage and the inter-electrode current in the case where the $SO_2$ concentration in the measured gas is 300 ppm. Further, the two-dot chain line L4 in FIG. 4 shows the relationship between the applied voltage and the inter-electrode current when the $SO_2$ concentration in the measured gas is 500 ppm. In these cases as well, in the region where the applied voltage is less than about 0.6V, in the same way as the case of the solid line L1 and broken line L2, the inter-electrode current becomes substantially 0. On the other hand, when the applied voltage is about 0.6V or more, inter-electrode current flows due to the decomposition of water. However, the higher the concentration of $SO_2$ in the measured gas, the smaller the inter-electrode current and the smaller the rate of increase of the inter-electrode current with respect to the applied voltage (slopes of one-dot chain line L3 and two-dot chain line L4).

In this way, from the example shown in FIG. 4 as well, it will be understood that the magnitude of the inter-electrode current when the applied voltage is the decomposition start voltage of water and $SO_X$ of about 0.6V or more changes according to the concentration of $SO_2$ (that is, $SO_X$) contained in the measured gas. For example, if plotting the magnitude of the inter-electrode current at the lines L1 to L4 when the applied voltage in the graph shown in FIG. 4 is 1.0V with respect to the concentration of $SO_2$ in the measured gas, the graph shown in FIG. 5 is obtained.

Figure 5:
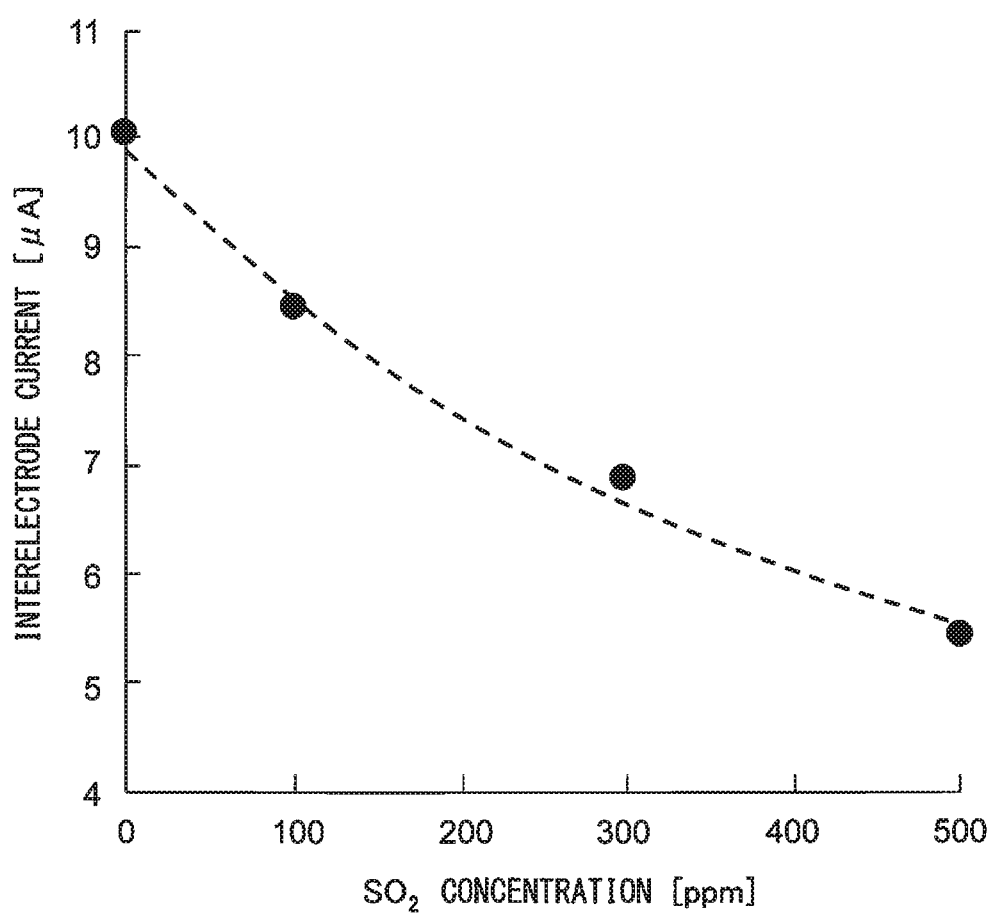
FIG. 5 is a graph showing a relationship between a magnitude of inter-electrode current and a sulfur oxide concentration in a measured gas when an applied voltage is 1.0V.

As will be understood from FIG. 5, the magnitude of the inter-electrode current when applying a predetermined voltage (in the example shown in FIG. 5, 1.0V) changes in accordance with the concentration of $SO_2$ contained in the measured gas (that is, $SO_X$). Therefore, it has been considered to be able to detect the $SO_X$ concentration based on the inter-electrode current when applying a predetermined voltage of the decomposition start voltage of the water and $SO_X$ or more.

However, the above-mentioned method of detection of the $SO_X$ concentration has the following problems. In the first electrochemical cell 51, as explained above, a predetermined voltage of the decomposition start voltage of the water and $SO_X$ (below, also simply referred to as the "decomposition start voltage") or more is applied between the first electrode 41 and the second electrode 42 so as to detect the decomposition current of the water flowing between the first electrode 41 and the second electrode 42. For this reason, even if the $SO_X$ concentration in the measured gas is the same, if the water concentration in the measured gas differs, a different inter-electrode current is detected from the first electrochemical cell 51. Specifically, if the water concentration in the measured gas becomes higher, the amount of water decomposed on the first electrode 41 increases, so the inter-electrode current becomes larger. On the other hand, if the water concentration in the measured gas becomes lower, the amount of water decomposed on the first electrode 41 decreases, so the inter-electrode current becomes smaller.

Therefore, if the water concentration in the measured gas differs, even if the $SO_X$ concentration in the measured gas is the same, the detected inter-electrode current fluctuates. As a result, the relationship between the inter-electrode current and the $SO_X$ concentration shown in FIG. 5 changes. For this reason, to precisely detect the $SO_X$ concentration in the measured gas, it was necessary that the water concentration in the measured gas be maintained in a predetermined range during detection of the $SO_X$ concentration.

Further, the decomposition start voltage of the water and $SO_X$ is higher than the decomposition start voltage of oxygen. For this reason, when the measured gas reaching the first electrochemical cell 51 contains oxygen, not only the decomposition current of water, but also the decomposition current of oxygen flows between the first electrode 41 and the second electrode 42. For this reason, even if the $SO_X$ concentration in the measured gas is the same, if the oxygen concentration in the measured gas differs, a different inter-electrode current will be detected from the first electrochemical cell 51. Specifically, if the oxygen concentration in the measured gas becomes higher, the amount of oxygen decomposed on the first electrode 41 increases, so the inter-electrode current becomes larger. On the other hand, if the oxygen concentration in the measured gas becomes lower, the amount of the oxygen decomposed on the first electrode 41 decreases, so the inter-electrode current becomes smaller.

Therefore, if the oxygen concentration in the measured gas differs, even if the $SO_X$ concentration in the measured gas is the same, the detected inter-electrode current fluctuates. As a result, the relationship between the inter-electrode current and $SO_X$ concentration shown in FIG. 5 changes. For this reason, to precisely detect the $SO_X$ concentration in the measured gas, the oxygen concentration in the measured gas has to be maintained in a predetermined range during detection of the $SO_X$ concentration.

Further, the $SO_X$ detection system 1, in particular the element part 10, gradually deteriorates along with use and sometimes changes in characteristics. In this case as well, the relationship between the inter-electrode current and $SO_X$ concentration shown in FIG. 5 changes. Further, even if the $SO_X$ detection system 1 does not deteriorate, due to individual differences in the $SO_X$ detection system 1, the relationship between the inter-electrode current and the $SO_X$ concentration changes.

Further, the detected inter-electrode current also changes depending on the temperature of the element part 10. The temperature of the element part 10 is controlled based on the impedance of the element part 10 by the heater control part 80c to a predetermined activation temperature. However, the relationship between the impedance and temperature of the element part 10 changes depending on individual differences of the element part 10. Therefore, even if the temperature of the element part 10 is controlled by the heater control part 80c, due to individual differences of the element part 10, the temperature of the element part 10 at the time of detection of the $SO_X$ concentration fluctuates. As a result, the relationship between the inter-electrode current and $SO_X$ concentration shown in FIG. 5 changes.

Therefore, in the method of detecting the inter-electrode current when applying a voltage of the decomposition start voltage to the first electrochemical cell 51 for a predetermined time and using a map such as shown in FIG. 5 to calculate the $SO_X$ concentration based on the detected inter-electrode current, it is sometimes not possible to ensure the precision of detection of the $SO_X$ concentration.

Further, if gradually making the applied voltage rise over a long period of time to detect the $SO_X$ concentration (voltage raising sweep), the time of detection of the $SO_X$ concentration becomes longer. Therefore, it may be considered to shorten the time of detection of the $SO_X$ concentration by making the applied voltage rise in steps. However, in this method, making the applied voltage rapidly rise results in spike-like noise in the inter-electrode current.

Figure 6:
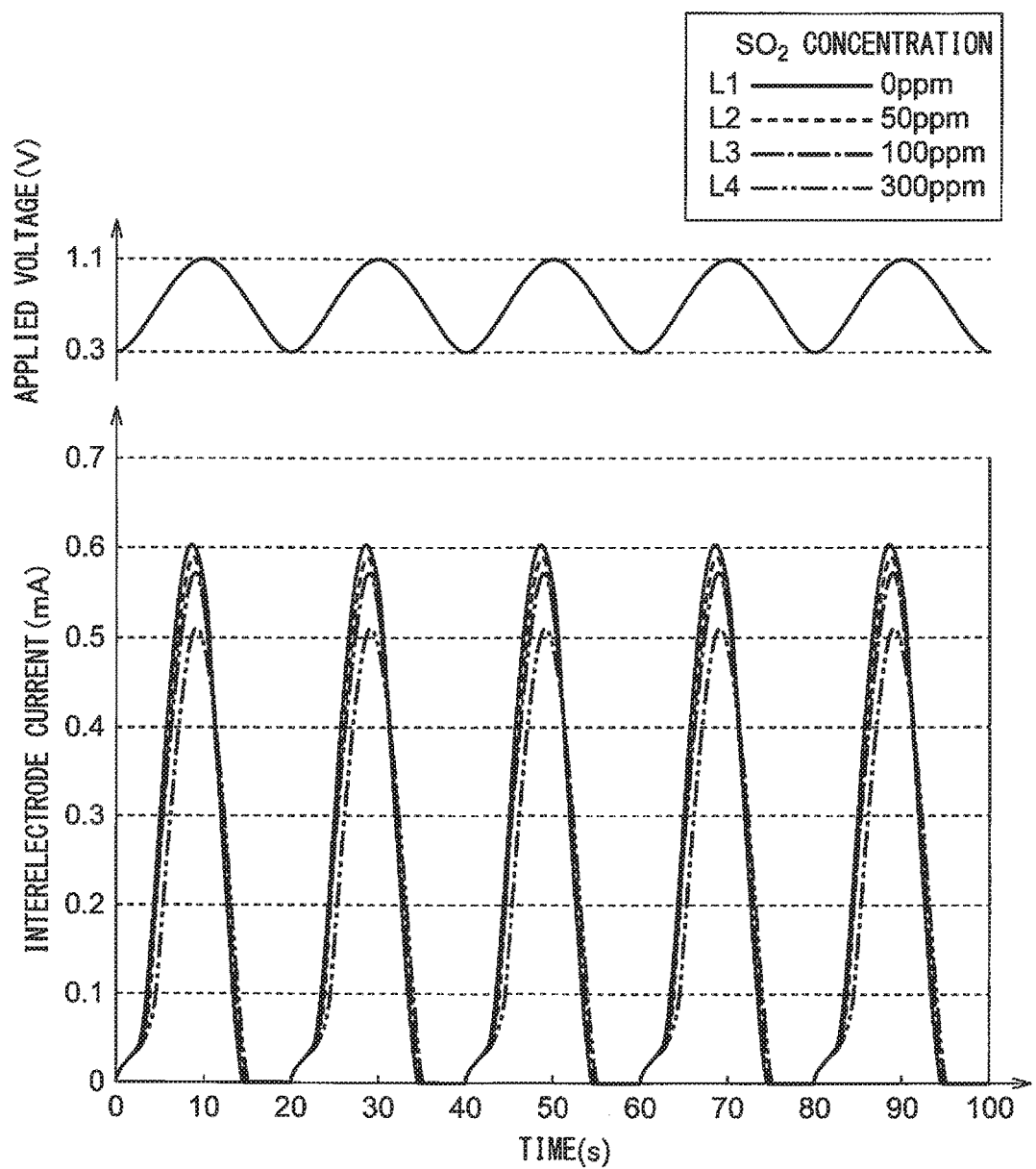
FIG. 6 is a timing diagram of an applied voltage and inter-electrode current when applying voltage to a first electrochemical cell by a voltage waveform of a sine wave having a 20 second period.

Therefore, the inventors of the present application discovered to apply a voltage to the first electrochemical cell 51 by a voltage waveform of a sine wave as the method of suppressing the occurrence of noise while shortening the time for detection of the $SO_X$ concentration. FIG. 6 is a timing diagram of the applied voltage and inter-electrode current when applying voltage to the first electrochemical cell 51 by a voltage waveform of a sine wave having a 20 second period (0.05 Hz frequency). In the illustrated example, four types of measured gases differing in concentrations of $SO_2$ (that is, $SO_X$) contained in the measured gas (0 ppm, 50 ppm, 100 ppm, and 300 ppm) were used. In FIG. 6, the solid line L1, broken line L2, one dot chain line L3, and two dot chain line L4 respectively show timing diagrams in the case of $SO_2$ concentrations in the measured gas of 0 ppm, 50 ppm, 100 ppm, and 300 ppm. In the illustrated example, the applied voltage is changed between a voltage less than the decomposition start voltage (0.3V) and a voltage higher than the decomposition start voltage (1.1V).

As will be understood from FIG. 6, the maximum value of the inter-electrode current detected when making the applied voltage rise from 0.3V to 1.1V by a voltage waveform of a sine wave having a period of 20 seconds changes according to the concentration of $SO_2$ (that is, $SO_X$) contained in the measured gas. However, in this case as well, the oxygen concentration and water concentration in the measured gas and deterioration and individual differences of the $SO_X$ detection system 1 cause the relationship between the maximum value of the detected inter-electrode current and the $SO_X$ concentration in the measured gas to change.

Figure 7:
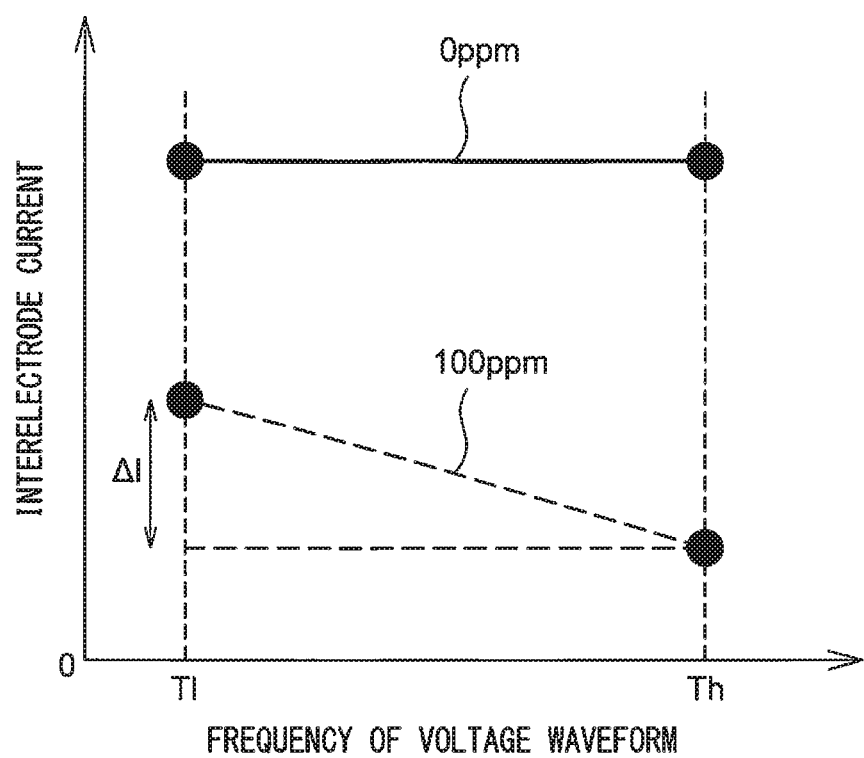
FIG. 7 is a graph showing a relationship between a period of a voltage waveform and inter-electrode current when applying voltage to a first electrochemical cell by a voltage waveform of a sine wave changing between 0.3V and 1.1V.

Below, referring to FIG. 7, the principle of detection of the $SO_X$ concentration in the present embodiment will be explained. FIG. 7 is a graph showing the relationship between the period of the voltage waveform and inter-electrode current (maximum value) when applying voltage to the first electrochemical cell 51 by a voltage waveform of a sine wave changing between 0.3V and 1.1V. In the illustrated graph, the maximum values of the inter-electrode current when the period of the voltage waveform is the short period Tl and long period Th are plotted. Note that, the longer the period of the voltage waveform, the longer the time during which a voltage of a decomposition start voltage (about 0.6V) or more is applied to the first electrochemical cell 51.

In the illustrated example, two types of measured gases differing in concentrations of $SO_2$ (that is, $SO_X$) contained in the measured gas (0 ppm and 100 ppm) were used. In FIG. 7, the solid line and broken line respectively show the relationships between the period of the voltage waveform and inter-electrode current (maximum value) when the $SO_2$ concentrations in the measured gas are 0 ppm and 100 ppm.

When the measured gas contains a predetermined amount of $SO_X$, basically the longer the time the voltage of the decomposition start voltage or more is applied to the first electrochemical cell 51, the smaller the maximum value of the detected inter-electrode current. The reason why is that the longer the time that the voltage of the decomposition start voltage or more is applied to the first electrochemical cell 51, the larger the amount of decomposition products of $SO_X$ adsorbed at the first electrode 41 due to decomposition of $SO_X$ and the larger the amount of drop of the decomposition current of water. For this reason, as shown by the broken line of FIG. 7, when the $SO_2$ (that is, $SO_X$) concentration in the measured gas is 100 ppm, the inter-electrode current at the long period Th becomes smaller than the inter-electrode current at the short period Tl.

On the other hand, when the $SO_2$ concentration in the measured gas is 0 ppm, the inter-electrode current at the long period Th is substantially equal to the inter-electrode current at the short period Tl. The reason why is that when the measured gas does not contain any $SO_X$, the decomposition products of $SO_X$ due to the decomposition of $SO_X$ are not adsorbed at the first electrode 41, so the decomposition current of water does not fall.

As explained above, the water concentration and oxygen concentration in the measured gas and deterioration and individual differences of the $SO_X$ detection system 1 cause the inter-electrode currents at the long period Th and short period Tl to fluctuate in some cases. However, by calculating the difference ΔI between the inter-electrode current at the long period Th and the inter-electrode current at the short period Tl, it is possible to cancel out the amount of fluctuation of the inter-electrode currents and extract the amount of drop of the decomposition current of water decreased due to the decomposition of $SO_X$. Therefore, by estimating the $SO_X$ concentration in the measured gas based on the difference ΔI between the inter-electrode current detected when applying voltage to the first electrochemical cell 51 by a voltage waveform of a long period and the inter-electrode current detected when applying voltage to the first electrochemical cell 51 by a voltage waveform of a short period, it is possible to improve the precision of detection of the $SO_X$ concentration. However, if consecutively applying voltage by the voltage waveform of a long period and applying voltage by the voltage waveform of a short period, the detected inter-electrode current is affected by sulfur poisoning of the electrodes.

Below, sulfur poisoning of the electrodes will be explained. As explained above, if applying the voltage of the decomposition start voltage or more to the first electrochemical cell 51, decomposition products of $SO_X$ (for example, sulfur and sulfur compounds) are adsorbed at the first electrode 41 of the first electrochemical cell 51. As a result, the first electrode 41 is poisoned by sulfur. For this reason, if again trying to detect the $SO_X$ concentration in the state where decomposition products of $SO_X$ are adsorbed at the first electrode 41, the detected inter-electrode current is affected by the decomposition products adsorbed on the first electrode 41. Specifically, sometimes the detected inter-electrode current becomes smaller than the value corresponding to the $SO_X$ concentration contained in the measured gas. For this reason, to precisely detect the $SO_X$ concentration in the measured gas, it is necessary to detect the $SO_X$ concentration in the state removing the decomposition products of $SO_X$ adsorbed at the first electrode 41.

According to the above-mentioned oxygen pumping action, it was explained that if applying voltage to the two sides of the solid electrolyte layer of the electrochemical cell, oxide ions are conducted from the cathode side to the anode side. However, if applying voltage to the two sides of the solid electrolyte layer of the electrochemical cell, if the inside of the measured gas chamber at the cathode side is a rich air-fuel ratio and the oxygen concentration contained in the measured gas is extremely small, rather oxide ions move from the anode side to the cathode side.

The reason which such movement of oxide ions occurs will be explained. If a difference in oxygen concentration occurs between the two side surfaces of the solid electrolyte layer, an electromotive force is generated (oxygen cell action) causing the oxide ions to move from the high concentration side surface side to the low concentration side surface side. As opposed to this, as explained above, if applying voltage between electrodes at the two sides of the solid electrolyte layer, even if the above-mentioned such electromotive force is generated, oxide ions move so that the potential difference between these electrodes becomes equal to the applied voltage.

As a result, if applying voltage between the electrodes arranged at the two sides of the solid electrolyte layer of the electrochemical cell, oxide ions move so that the difference in oxygen concentration on the two electrodes becomes a difference in concentration corresponding to the potential difference of the two electrodes. Specifically, oxide ions move so that the oxygen concentration on the anode becomes higher than the oxygen concentration on the cathode by exactly the difference in concentration corresponding to the potential difference.

For this reason, if applying a certain voltage between the two electrodes of the electrochemical cell, when the oxygen concentration on the anode is not higher than the oxygen concentration on the cathode by the difference of concentration corresponding to this certain voltage, oxide ions move from the cathode to the anode so that the difference in oxygen concentration becomes larger. As a result, the oxygen concentration on the cathode falls and the difference in oxygen concentration on the two electrodes approaches the concentration corresponding to this certain voltage. Conversely, when the oxygen concentration on the anode is higher compared with the oxygen concentration on the cathode by the difference in concentration corresponding to this voltage, oxide ions move from the anode to the cathode so that the difference in oxygen concentration becomes smaller. As a result, the oxygen concentration on the cathode rises and the difference in oxygen concentration on the two electrodes approaches the difference in concentration corresponding to the above certain voltage.

Here, when the potential difference between electrodes arranged at the two side surfaces of the solid electrolyte layer is 0.45V, the difference of concentration corresponding to this potential difference becomes equal to the difference in concentration between the oxygen concentration contained in the atmosphere and the oxygen concentration in the equilibrium state (that is, the state with no excess unburned components (HC, CO, etc.) or excess oxygen or the state where the air-fuel ratio is the stoichiometric air-fuel ratio). Therefore, when the anode of the electrochemical cell is exposed to the atmosphere and the cathode is exposed to the measured gas, if applying a voltage of 0.45V between these electrodes, oxide ions move so that the surroundings of the cathode exposed to the measured gas chamber become the equilibrium state.

For this reason, when the oxygen concentration of the measured gas is higher than the oxygen concentration in the equilibrium state, that is, when the air-fuel ratio of the measured gas is leaner than the stoichiometric air-fuel ratio (case of a state where oxygen is in excess with respect to the unburned components), oxide ions move from the cathode to the anode in the measured gas chamber. As a result, the oxygen concentration of the measured gas approaches the oxygen concentration in the equilibrium state. On the other hand, when the oxygen concentration of the measured gas is lower than the oxygen concentration in the equilibrium state, that is, when the air-fuel ratio of the measured gas is richer than the stoichiometric air-fuel ratio (case of a state where unburned components are in excess with respect to oxygen), oxide ions move from the anode to the cathode in the measured gas chamber. As a result, the oxygen concentration of the measured gas approaches the oxygen concentration in the equilibrium state.

On the other hand, when the potential difference between electrodes arranged at the two side surfaces of the solid electrolyte layer is less than 0.45V, the difference of concentration corresponding to this potential difference becomes smaller than the difference of concentration between the oxygen concentration in the atmosphere and the oxygen concentration in the equilibrium state. Therefore, when the anode of the electrochemical cell is exposed to the atmosphere and the cathode is exposed to the measured gas, if applying a voltage of less than 0.45V between these electrodes, oxide ions move so that the cathode exposed to the measured gas becomes a slight oxygen excess from the equilibrium state. As a result, the cathode of the electrochemical cell is maintained in the state of slight oxygen excess compared with the equilibrium state.

Therefore, if applying less than 0.45V of voltage between the first electrode 41 and the second electrode 42 of the first electrochemical cell 51 using the first electrode 41 as the cathode and the second electrode as the anode, the first electrode 41 is maintained in a state of a slight oxygen excess. Even when decomposition products of $SO_X$ are adsorbed on the first electrode 41, if the first electrode 41 is maintained in a state of oxygen excess, the adsorbed decomposition products react with the oxygen to become $SO_X$ and are desorbed from the first electrode 41. Therefore, when decomposition products of $SO_X$ are adsorbed on the first electrode 41 along with the $SO_X$ detection processing, by making the voltage applied to the first electrochemical cell 51 less than 0.45V, it is possible to make the decomposition products desorb from the first electrode 41.

Therefore, in the present embodiment, to reduce the effect of sulfur poisoning of the electrodes, poisoning recovery control for making the decomposition products of $SO_X$ desorb from the first electrode is performed between application of voltage by a voltage waveform of a long period and application of voltage by a voltage waveform of a short period.

If making the voltage applied to the first electrochemical cell 51 less than 0.45V, it is possible to promote the desorption of the decomposition product. However, if excessively reducing the applied voltage, blackening easily occurs at the first solid electrolyte layer 11. Here, "blackening" is the phenomenon where the metal oxide contained in the solid electrolyte layer is reduced and metal is produced at the solid electrolyte layer. If the first solid electrolyte layer 11 blackens, the ion conductivity of the first solid electrolyte layer 11 deteriorates and $SO_X$ can no longer be suitably detected. For this reason, the voltage applied to the first electrochemical cell 51 is preferably made a voltage higher than the applied voltage where blackening occurs (for example, −2.0V).

Figure 8:
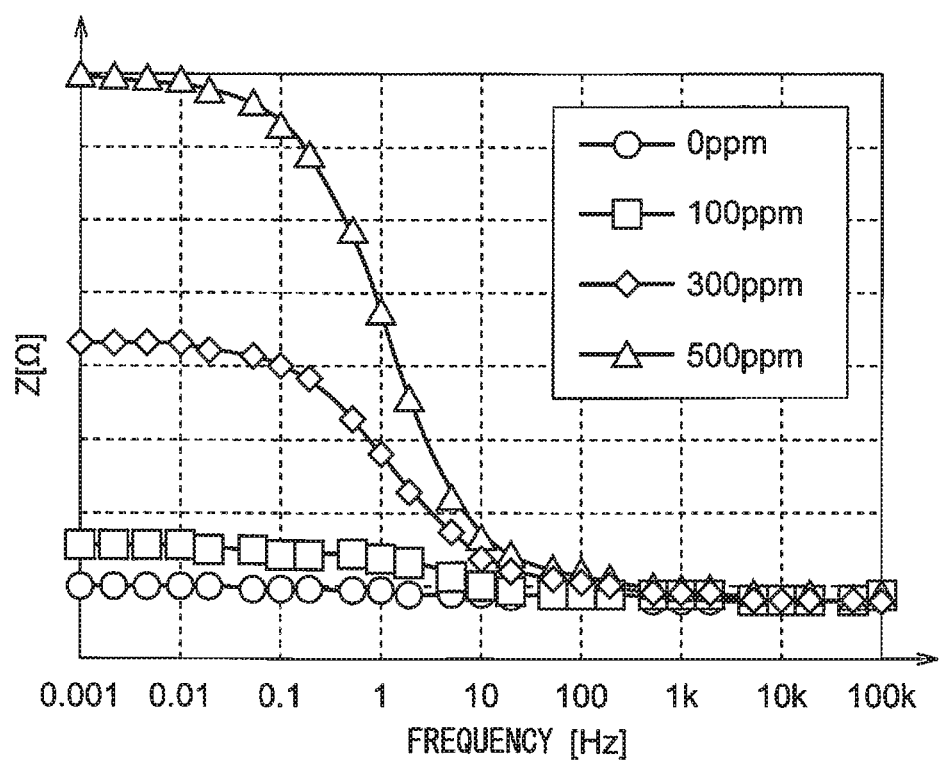
FIG. 8 is a graph showing a relationship between an impedance of the first electrochemical cell and a frequency of a sine wave when applying voltage of the sine wave to the first electrochemical cell.

Further, the inventors of the present application measured the impedance characteristic of the first electrochemical cell 51 so as to find the suitable period of the voltage waveform of the applied voltage. FIG. 8 is a graph showing the relationship between the impedance of the first electrochemical cell 51 and frequency of the sine wave when applying a voltage of the sine wave (0.7V±0.4V) to the first electrochemical cell 51. In the illustrated example, four types of measured gases differing in concentrations of $SO_2$ (that is, $SO_X$) contained in the measured gas (0 ppm, 100 ppm, 300 ppm, and 500 ppm) were used. The data plotted by the circles, squares, diamonds, and triangles respectively show the relationships between impedance and frequency in the cases of $SO_2$ concentrations of 0 ppm, 100 ppm, 300 ppm, and 500 ppm.

If the frequency of the applied voltage is relatively high, the impedance of the first electrochemical cell 51 shows substantially the same value regardless of the value of the $SO_2$ concentration. In this case, the time when the applied voltage is the decomposition start voltage or more is short, and thus it is considered that almost no decomposition products of $SO_X$ formed due to decomposition of $SO_X$ are adsorbed at the first electrode 41. On the other hand, if the frequency of the applied voltage is relatively low, the impedance of the first electrochemical cell 51 becomes a value corresponding to the value of the $SO_2$ concentration. In this case, it is considered that decomposition products of $SO_X$ formed due to decomposition of $SO_X$ are adsorbed at the first electrode 41.

As will be understood from FIG. 8, in the region where the frequency of the applied voltage is 10 Hz or less, a certain extent of difference occurs in the value of the impedance with respect to the $SO_2$ concentration. For this reason, in this region, the inter-electrode current corresponding to the $SO_X$ concentration can be detected and in turn the $SO_X$ concentration in the measured gas can be detected.

Further, to shorten the detection time of the $SO_X$ concentration, it is preferable to make the frequency of the applied voltage as high as possible. As will be understood from FIG. 8, in the region where the frequency of the applied voltage is less than 0.01 Hz, the value of the impedance is substantially saturated. A frequency of 10 Hz corresponds to a period of 0.1 second, while a frequency of 0.01 Hz corresponds to a period of 100 seconds. For this reason, in the present embodiment, to detect the $SO_X$ concentration in the measured gas, the voltage waveform of the voltage applied to the first electrochemical cell 51 is set to a sine wave having a period of 0.1 second to 100 second.

Figure 9:
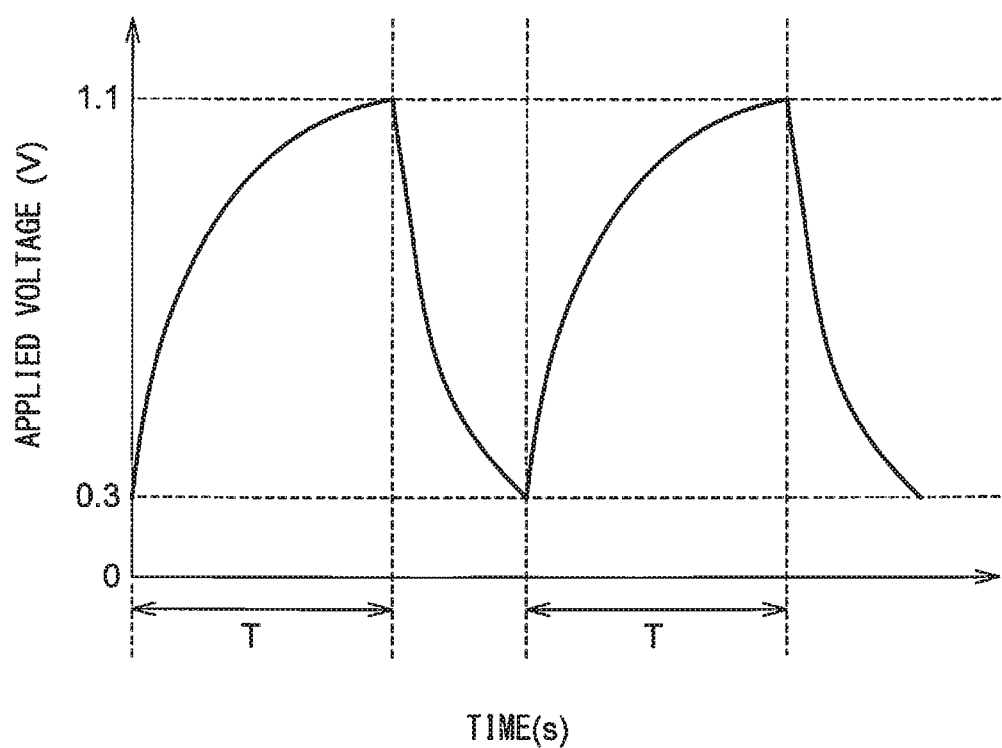
FIG. 9 is a timing diagram of applied voltage showing a voltage waveform of a square wave having a predetermined time constant.

Note that, as shown in FIG. 9, the square wave having the predetermined time constant T has a waveform similar to a sine wave. A period of 100 seconds corresponds to a time constant of 50 seconds, while a period of 0.1 second corresponds to a time constant of 0.05 second. For this reason, in the present embodiment, to detect the $SO_X$ concentration in the measured gas, it is also possible to set the voltage waveform of the inter-electrode voltage applied to the first electrochemical cell 51 to a square wave having a time constant of 0.05 second to 50 second. For example, it is possible to suitably set the cutoff frequency of the low pass filter (LPF) provided at the voltage application circuit 61 to set the desired time constant. In this case, the step-like digital signal output by the ECU 80 passes through the DA converter 63 and LPF and is converted to a signal having the desired time constant. Note that, in this Description, "the time constant of the square wave when raising the voltage from the first voltage to the second voltage" means the time T from when the voltage starts to rise from the first voltage to when it reaches the second voltage. Further, "the time constant of the square wave when lowering the voltage from the second voltage to the first voltage" means the time from when the voltage starts to be lowered from the second voltage to when it reaches the first voltage.

In the present embodiment, the $SO_X$ concentration in the measured gas is detected as follows. The voltage control part 80b of the ECU 80 first performs first control for making the voltage applied to the first electrochemical cell 51 rise from the first voltage to the second voltage so that the voltage of the decomposition start voltage or more is applied to the first electrochemical cell 51 for a first period of time. The first voltage is a voltage less than the decomposition start voltage, for example, is 0.3V which is less than 0.6V. The second voltage is a voltage higher than the decomposition start voltage, for example, is 1.1V which is higher than 0.6V.

Further, the voltage control part 80b makes the voltage applied to the first electrochemical cell 51 rise from the first voltage to the second voltage by a voltage waveform of a sine wave having the first period in the first control. The first period is a period of 0.1 second to 100 seconds, for example, is 1 second.

The voltage control part 80b performs second control for making the voltage applied to the first electrochemical cell 51 rise from the first voltage to the second voltage after first control so that a voltage of the decomposition start voltage or more is applied to the first electrochemical cell 51 for a second period of time. The second period of time is a time different from the first period of time.

Further, the voltage control part 80b, in the second control, makes the voltage applied to the first electrochemical cell 51 rise from the first voltage to the second voltage by a voltage waveform of a sine wave having a second period. The second period is 0.1 second to 100 seconds or a period different from the first period. For example, the second period is a period longer than the first period, that is, 5 seconds. In this case, the second period of time becomes longer than the first period of time. Note that, the second period may be shorter than the first period. For example, the first period may be 5 seconds and the second period may be 1 second. In this case, the second period of time becomes shorter than the first period of time.

Further, the voltage control part 80b performs poisoning recovery control applying a voltage enabling desorption of decomposition products of $SO_X$ adsorbed at the first electrode 41 to the first electrochemical cell 51 between the first control and second control so as to cause desorption of decomposition products of $SO_X$ adsorbed at the first electrode 41 due to the first control. The voltage enabling desorption of decomposition products of $SO_X$ adsorbed at the first electrode 41 is for example 0.3V which is less than 0.45V.

Note that, the voltage control part 80b may cause the voltage applied to the first electrochemical cell 51 to rise from the first voltage to the second voltage by a voltage waveform of a square wave having a first time constant in the first control and cause the voltage applied to the first electrochemical cell 51 to rise from the first voltage to the second voltage by a voltage waveform of a square wave having a second time constant in the second control.

The first time constant is a time constant of 0.05 second to 50 seconds, for example, 0.5 second. Further, the second time constant is a time constant of 0.05 second to 50 seconds and a time constant different from the first time constant. For example, the second time constant is a time constant longer than the first time constant, that is, 2.5 seconds. In this case, the second period of time becomes longer than the first period of time. Note that, the second time constant may be shorter than the first time constant. For example, the first time constant may be 2.5 seconds, while the second time constant may be 0.5 second. In this case, the second period of time becomes shorter than the first period of time.

The estimating part 80a of the ECU 80 estimates the $SO_X$ concentration in the measured gas based on the difference (absolute value) between the first current detected by the current detection circuit 62 when the first control is performed and the second current detected by the current detection circuit 62 when the second control is performed. For example, the estimating part 80a estimates that the $SO_X$ concentration in the measured gas is the reference concentration or more when the difference between the first current and the second current is the reference value or more. The reference concentration is, for example, made a value corresponding to the lower limit value of the content of the sulfur component in the fuel which may have a detrimental effect on the functions of the internal combustion engine. The reference concentration is determined in advance by experiments or calculations. Further, the reference value is determined in advance by experiments or calculations based on the reference concentration.

For example, the first current is the maximum value of the current detected by the current detection circuit 62 when the first control is performed, while the second current is the maximum value of the current detected by the current detection circuit 62 when the second control is performed. Note that, the first current may be the current detected when the applied voltage reaches the second voltage by the first control, while the second current may be the current detected when the applied voltage reaches the second voltage by the second control. Further, the first current may be the cumulative value of the current detected during the first control, while the second current may be the cumulative value detected during the second control. Further, the first current may be the cumulative value of the current detected when a voltage of the decomposition start voltage or more is applied by the first control, while the second current may be the cumulative value of the current detected when a voltage of the decomposition start voltage or more is applied by the second control.

The water concentration and oxygen concentration in the measured gas and deterioration and individual differences of the $SO_X$ detection system 1 cause the values of the inter-electrode current detected at the first control and second control to change. However, by calculating the difference between the first current detected at the first control and the second current detected at the second control, it is possible to cancel out the amount of fluctuation of the inter-electrode current and extract the amount of drop of the decomposition current of water decreased due to the decomposition of $SO_X$.

Therefore, in the present embodiment, by estimating the $SO_X$ concentration in the measured gas based on the difference between the first current and the second current, it is possible to improve the precision of detection of the $SO_X$ concentration in the measured gas (exhaust gas).

Further, there is an upper limit concentration able to be detected by the $SO_X$ detection system 1. If the $SO_X$ concentration is the upper limit concentration or more, the adsorption of the decomposition products of $SO_X$ at the first electrode 41 reaches the saturated state, so the inter-electrode current does not change much at all in accordance with the $SO_X$ concentration. For this reason, the estimating part 80a estimates that the $SO_X$ concentration in the measured gas is the upper limit concentration or more when the first current is the lower limit value or less. In this case, it is possible to quickly estimate the $SO_X$ concentration in the measured gas without performing the poisoning recovery control and second control. The upper limit concentration is for example 500 ppm. The lower limit value is made a value corresponding to the current value detected in the case where the first control is performed when the $SO_X$ concentration in the measured gas is the upper limit concentration or more. The lower limit value is determined in advance by experiments or calculations.

Note that, the estimating part 80a may estimate that the $SO_X$ concentration in the measured gas is the upper limit concentration or more when the first current is a first lower limit value or less and the second current is a second lower limit value or less. Due to this, it is possible to more precisely detect when the $SO_X$ concentration in the measured gas is the upper limit concentration or more. The first lower limit value is a value similar to the above lower limit value. The second lower limit value is made a value corresponding to the current value detected in the case where the second control is performed when the $SO_X$ concentration in the measured gas is the upper limit concentration or more. The second lower limit value is determined in advance by experiments or calculations.

Further, the estimating part 80a may estimate the $SO_X$ concentration in the measured gas based on the ratio of the first current and the second current. For example, the estimating part 80a estimates that the $SO_X$ concentration in the measured gas is the reference concentration or more when the ratio of the first current and the second current is the reference value or more. At this time, the ratio of the first current and the second current is calculated by dividing the first current by the second current when the first period of time is shorter than the second period of time and is calculated by dividing the second current by the first current when the first period of time is longer than the second period of time. Further, the estimating part 80a may estimate that the $SO_X$ concentration in the measured gas is the reference concentration or more when the ratio of the first current and the second current is the reference value or less. At this time, the ratio of the first current and the second current is calculated by dividing the second current by the first current when the first period of time is shorter than the second period of time and is calculated by dividing the first current by the second current when the first period of time is longer than the second period of time. The reference concentration is, for example, made a value corresponding to the lower limit value of the content of the sulfur components in the fuel which might have a detrimental effect on the functions of the internal combustion engine. The reference concentration is determined in advance by experiments or calculations. Further, the reference value is determined in advance by experiments or calculations based on the reference concentration.

Further, the estimating part 80a may estimate the $SO_X$ concentration in the measured gas based on the difference or ratio of other parameters calculated from the first current and the second current. For example, the estimating part 80a may estimate the $SO_X$ concentration in the measured gas based on the difference or ratio of resistances between electrodes calculated from the first current and the second current. The resistances between electrodes are calculated from the first current and the second current and the difference or ratio of the resistances between electrodes is correlated with the difference or ratio of the first current and the second current, so in this case as well, it can be said that the estimating part 80a estimates the $SO_X$ concentration in the measured gas based on the difference or ratio of the first current and the second current.

Figure 10:
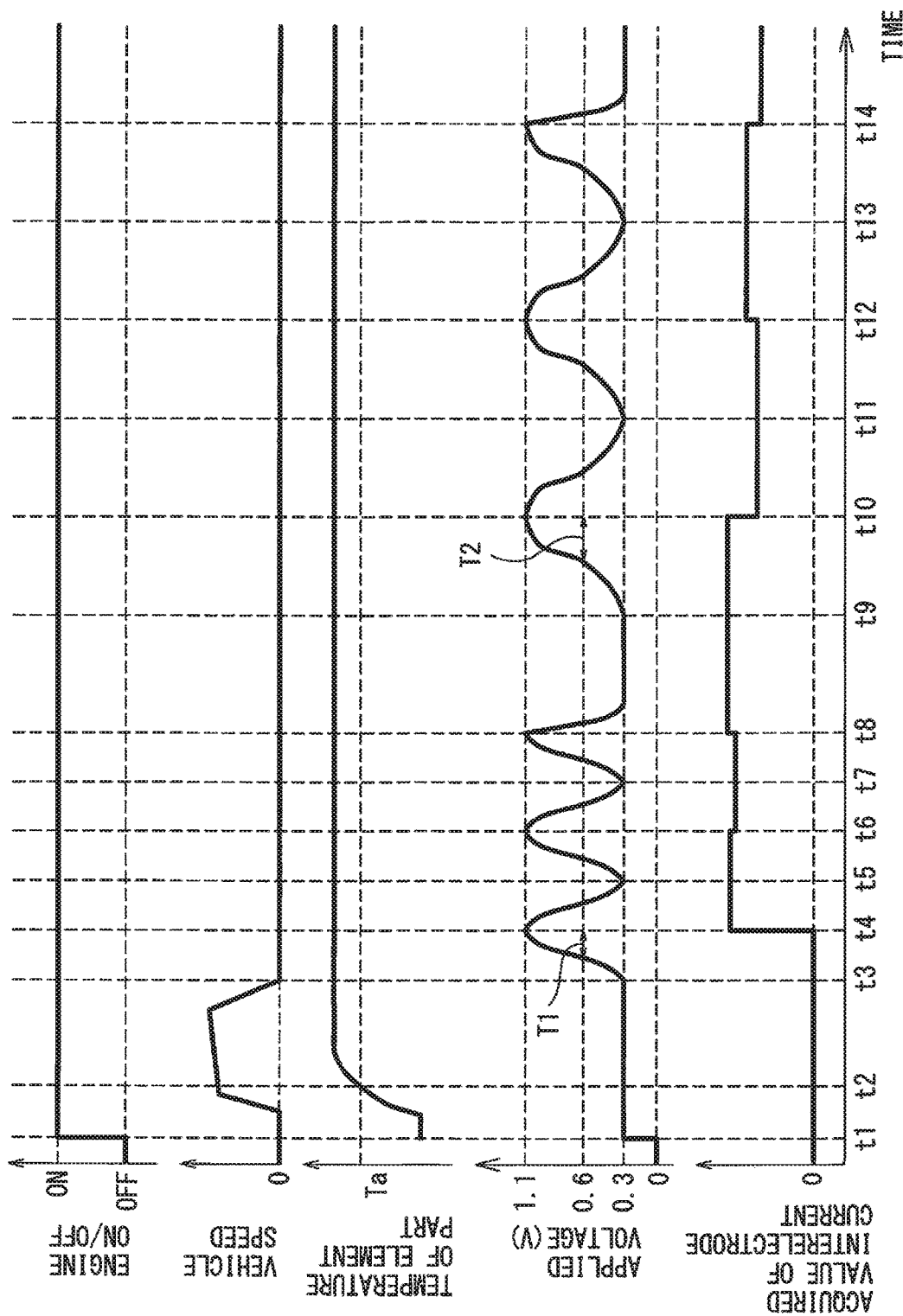
FIG. 10 is a timing diagram of an on/off state of an engine etc. when detecting a $SO_X$ concentration in the measured gas.

Below, referring to the timing diagram of FIG. 10, control for detecting the $SO_X$ concentration will be specifically explained. FIG. 10 is a schematic timing diagram of the on/off state of the engine (internal combustion engine), vehicle speed, temperature of the element part 10, voltage applied to the first electrochemical cell 51, and the acquired values of inter-electrode current when detecting the $SO_X$ concentration in the measured gas. In the illustrated example, the first control and second control are performed three times each for detecting the $SO_X$ concentration.

In the illustrated example, at the time t1, the ignition key is turned on and the engine (internal combustion engine) is started up. After the startup of the engine, the voltage applied to the first electrochemical cell 51 is set to 0.3V so that the decomposition products of $SO_X$ which might be adsorbed at the first electrode 41 are desorbed from the first electrode 4. Further, at the time t1, the heater 55 of the element part 10 is turned on, while at the time t2, the temperature of the element part 10 reaches the activation temperature. After that, at the time t3, the vehicle speed of the vehicle in which the engine is mounted becomes zero and the operating state of the engine becomes the idle state. At the time t3, the operating state of the engine is the idle state and the element part 10 is in the active state, so in the illustrated example, the condition for detection of the $SO_X$ concentration is satisfied.

As a result, at the time t3, the first cycle of the first control is performed. Specifically, from the time t3 to the time t4, the voltage applied to the first electrochemical cell 51 is made to rise from 0.3V to 1.1V by a voltage waveform of a sine wave having the first period. As a result, a voltage of the decomposition start voltage (about 0.6V) or more is applied to the first electrochemical cell 51 for the first period of time T1.

If the first control is ended at the time t4, the maximum value of the inter-electrode current detected during the first control is acquired. After the time t4, the applied voltage is made to fall from 1.1V to 0.3V. The voltage waveform at this time is also a sine wave having the first period. At the time t5, the second cycle of the first control is performed and at the time t6 the maximum value of the inter-electrode current detected during the second cycle of the first control is acquired. At the time t6 to the time t8 as well, voltage control the same as the time t4 to the time t6 is performed. As a result, at the time t8, the maximum value of the inter-electrode current detected during the third cycle of the first control is acquired.

After the time t8, poisoning recovery control is performed. Specifically, a voltage of 0.3V is applied to the first electrochemical cell 51 for a predetermined time so as to desorb the decomposition products of $SO_X$ adsorbed at the first electrode 41 due to the first control.

After the poisoning recovery control, the first cycle of second control is performed at the time t9. Specifically, the voltage applied to the first electrochemical cell 51 is made to rise from 0.3V to 1.1V from the time t9 to the time t10 by a voltage waveform of a sine wave having a second period. As a result, a voltage of the decomposition start voltage (about 0.6V) or more is applied to the first electrochemical cell 51 for the second period of time T2. In the illustrated example, the second period is longer than the first period. For this reason, the second period of time T2 becomes longer than the first period of time T1.

If the second control ends at the time t10, the maximum value of the inter-electrode current detected during the second control is acquired. After the time t10, the applied voltage is made to fall from 1.1V to 0.3V. The voltage waveform at this time is also a sine wave having the second period. At the time t11, the second cycle of the second control is performed, while at the time t12, the maximum value of the inter-electrode current detected during the second cycle of the second control is acquired. At the time t12 to the time t14 as well, voltage control the same as the time t10 to the time t12 is performed. As a result, the maximum value of the inter-electrode current detected during the third cycle of the second control is acquired at the time t14.

After the time t14, a voltage of 0.3V is applied to the first electrochemical cell 51 so as to desorb the decomposition products of $SO_X$ adsorbed at the first electrode 41 due to the second control. Further, after the time t14, the $SO_X$ concentration in the measured gas is estimated based on the difference between the first current detected when the first control is performed and the second current detected when the second control is performed. The first current is made the average value of the maximum values of the inter-electrode current acquired three times at the first control. The second current is made the average value of the maximum values of the inter-electrode current acquired three times at the second control.

In the illustrated example, the first period of time T1 is shorter than the second period of time T2. In this case, the decomposition products of $SO_X$ adsorbed at the first electrode 41 by the first control basically becomes smaller than the decomposition products of $SO_X$ adsorbed at the first electrode 41 by the second control. For this reason, it is possible to shorten the time of the poisoning recovery control performed between the first control and the second control. As a result, if performing the first control and second control so that the first period of time T1 becomes shorter than the second period of time T2, it is possible to shorten the $SO_X$ detection time (time from t3 to t10 at FIG. 10) compared with when performing the first control and second control so that the first period of time T1 becomes longer than the second period of time T2.

Figure 11:
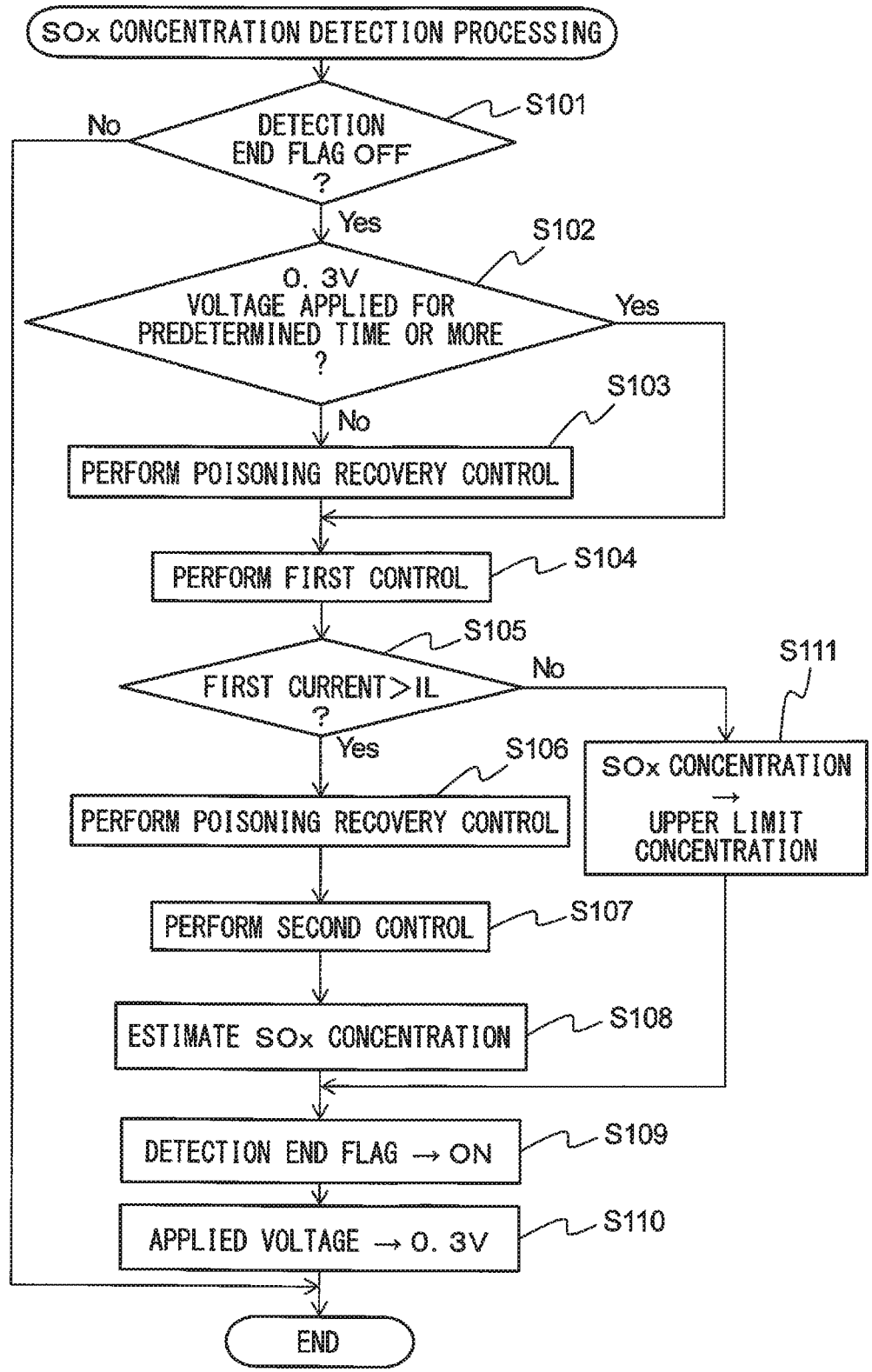
FIG. 11 is a flow chart of a control routine of $SO_X$ concentration detection processing in the first embodiment of the present invention.

Below, referring to the flow chart of FIG. 11, control for detecting the $SO_X$ concentration will be explained in detail. FIG. 11 is a flow chart of a control routine of $SO_X$ concentration detection processing in the first embodiment of the present invention. The control routine is repeatedly performed by the ECU 80. Further, the control routine is forcibly ended even if in the middle of proceeding if it is judged that the condition for detection of the $SO_X$ concentration is not satisfied in the later explained detection condition judgment processing.

First, at step S101, the estimating part 80a judges whether the detection completion flag is off. The detection completion flag is set off when the fuel tank 33 is being refilled with fuel and is set on when the $SO_X$ concentration in the measured gas has been estimated. Further, the detection completion flag may be set off when the ignition key is turned on or off. If at step S101 it is judged that the detection completion flag is on, the $SO_X$ concentration has already finished being detected, so the control routine ends. On the other hand, if at step S101 it is judged that the detection completion flag is off, the control routine proceeds to step S102.

At step S102, the voltage control part 80*b* judges whether a voltage enabling desorption of the decomposition products of the $SO_X$ adsorbed at the first electrode 41 has been applied for a predetermined time or more. The voltage enabling desorption of the decomposition products of the $SO_X$ adsorbed at the first electrode 41 is, for example, 0.3V. The predetermined time is made a time sufficient for desorption of the decomposition products of $SO_X$ adsorbed at the first electrode 41. If at step S102 it is judged that a voltage of 0.3V has not been applied for predetermined time or more, the control routine proceeds to step S103.

At step S103, the voltage control part 80*b* performs the poisoning recovery control. Specifically, the voltage control part 80*b* applies a voltage enabling desorption of the decomposition products of $SO_X$ adsorbed at the first electrode 41 to the first electrochemical cell 51 for a predetermined time. The voltage applied to the first electrochemical cell 51 is for example 0.3V. The predetermined time is made a time sufficient for desorption of decomposition products of $SO_X$ adsorbed at the first electrode 41. On the other hand, if at step S102 it is judged that a voltage of 0.3V is being applied for a predetermined time or more, the control routine skips step S103 and proceeds to step S104.

Next, at step S104, the voltage control part 80*b* performs the first control. Specifically, the voltage control part 80*b* makes the voltage applied to the first electrochemical cell 51 rise from the first voltage to the second voltage so that the voltage of the decomposition start voltage or more is applied to the first electrochemical cell 51 for the first period of time. The first voltage is a voltage of less than the decomposition start voltage, for example, 0.3V. The second voltage is a voltage higher than the decomposition start voltage, for example, 1.1V. Further, the voltage control part 80*b*, in the first control, makes the voltage applied to the first electrochemical cell 51 rise from the first voltage to the second voltage by a voltage waveform of a sine wave having a first period. The first period is a period of 0.1 second to 100 seconds, for example, 1 second. The current detection circuit 62*d* detects the inter-electrode current while the first control is being performed.

Next, at step S105, the estimating part 80*a* judges whether the first current detected by the current detection circuit 62 when the first control is performed is larger than the lower limit value IL. The first current is the maximum value of the current detected by the current detection circuit 62 when the first control is performed. The lower limit value IL is made a value corresponding to the current value detected when first control is performed when the $SO_X$ concentration in the measured gas is the upper limit concentration or more. The lower limit value IL is determined in advance by experiments or calculations. If at step S105 it is judged that the first current is larger than the lower limit value IL, the control routine proceeds to step S106.

At step S106, the voltage control part 80*b* performs poisoning recovery control to desorb the decomposition products of $SO_X$ adsorbed at the first electrode 41 due to the first control. Specifically, the voltage control part 80*b* applies a voltage able to desorb decomposition products of $SO_X$ adsorbed at the first electrode 41 to the first electrochemical cell 51 for a predetermined time. The applied voltage to the first electrochemical cell 51 is for example 0.3V. The predetermined time is made a time sufficient for desorption of the decomposition products of $SO_X$ adsorbed at the first electrode 41 by the first control.

Next, at step S107, the voltage control part 80*b* performs the second control. Specifically, the voltage control part 80*b* raises the voltage applied to the first electrochemical cell 51 from the first voltage to the second voltage so that voltage of the decomposition start voltage or more is applied to the first electrochemical cell 51 for the second period of time. Further, the voltage control part 80*b* makes the voltage applied to the first electrochemical cell 51 rise from the first voltage to the second voltage by a voltage waveform of a sine wave having a second period in the second control. The second period is a period of 0.1 second to 100 second different from the first period. For example, the second period is a period longer than the first period, that is, 5 seconds. The current detection circuit 62 detects the inter-electrode current while the second control is being performed.

Next, at step S108, the estimating part 80*a* estimates the $SO_X$ concentration in the measured gas based on the difference between the first current and the second current detected by the current detection circuit 62 when the second control is performed. The second current is a maximum value of the current detected by the current detection circuit 62 when the second control is performed. Specifically, the estimating part 80*a* estimates that the $SO_X$ concentration in the measured gas is a reference concentration or more when the difference between the first current and the second current is the reference value or more. The reference concentration is, for example, made a value corresponding to the lower limit value of the content of the sulfur components in the fuel which may have a detrimental effect on the functions of the internal combustion engine. The reference concentration is determined in advance by experiments or calculations. Further, the reference value is determined in advance by experiments or calculations based on the reference concentration.

The estimating part 80*a* may turn on a warning light of a vehicle mounting the internal combustion engine when estimating that the $SO_X$ concentration in the measured gas is the reference concentration or more. Further, when it is estimated that the $SO_X$ concentration in the measured gas is the reference concentration or more, control may be performed to restore the exhaust purification catalyst 28 from sulfur poisoning. Therefore, when a warning light informing the driver of a high content of sulfur in the fuel is turned on or when control performed when the content of sulfur in the fuel is high is performed, it can be said that the it is substantially estimated that $SO_X$ concentration in the measured gas is the reference concentration or more by the $SO_X$ detection system.

Next, at step S109, the detection completion flag is set on since the $SO_X$ concentration finishes being detected at step S108. Next, at step S110, the voltage control part 80*b* sets the voltage applied to the first electrochemical cell to 0.3V so as to desorb the decomposition products of $SO_X$ adsorbed at the first electrode 41 due to the second control. After step S110, the control routine is ended.

On the other hand, if at step S105 it is judged that the first current is the lower limit value or less, the control routine proceeds to step S111. At step S111, the estimating part 80*a* estimates that the $SO_X$ concentration in the measured gas is the upper limit concentration or more. The upper limit concentration is for example 500 ppm. The control routine proceeds to step S109 after step S111.

Note that, the second period may be made shorter than the first period so that the second period of time becomes shorter than the first period of time. Further, the voltage control part 80b may make the voltage applied to the first electrochemical cell 51 rise from the first voltage to the second voltage by a voltage waveform of a square wave having a first time constant at the first control of step S104 and may make the voltage applied to the first electrochemical cell 51 rise from the first voltage to the second voltage by a voltage waveform of a square wave having a second time constant at the second control of step S107. The first time constant is a time constant of 0.05 second to 50 seconds, for example, 0.5 second. Further, the second time constant is a time constant of 0.05 second to 50 seconds and a time constant different from the first time constant, for example, 2.5 seconds.

Further, the first current may be the current detected when the applied voltage reaches the second voltage by the first control, while the second current may be the current detected when the applied voltage reaches the second voltage by the second control. Further, the first current may be the cumulative value of the current detected during the first control, while the second current may be the cumulative value of the current detected during the second control. Further, the first current may be the cumulative value of the current detected while the voltage of the decomposition start voltage or more is being applied by the first control, while the second current may be the cumulative value of the current detected while the voltage of the decomposition start voltage or more is being applied by the second control.

Further, the estimating part 80a may judge, after step S107, whether the first current is the first lower limit value or less and the second current is the second lower limit value or less. In this case, step S105 is omitted. The first lower limit value is a value similar to the above-mentioned lower limit value at step S105. The second lower limit value is made a value corresponding to the current value detected when the second control is performed when the $SO_X$ concentration in the measured gas is the upper limit concentration or more. The second lower limit value is determined in advance by experiments or calculations. When it is judged that the first current is the first lower limit value or less and the second current is the second lower limit value or less, the control routine proceeds to step S111. On the other hand, when it is judged that the first current is larger than the first lower limit value or the second current is larger than the second lower limit value, the control routine proceeds to step S108.

Further, at step S108, the estimating part 80a may estimate the $SO_X$ concentration in the measured gas based on the ratio of the first current and the second current. Further, as shown in the timing diagram shown in FIG. 10, the first control at step S104 and the second control at step S107 may be performed for a plurality of times. In this case, the first current and the second current are respectively made average values of the current values detected for the times of the plurality of times.

Figure 12:
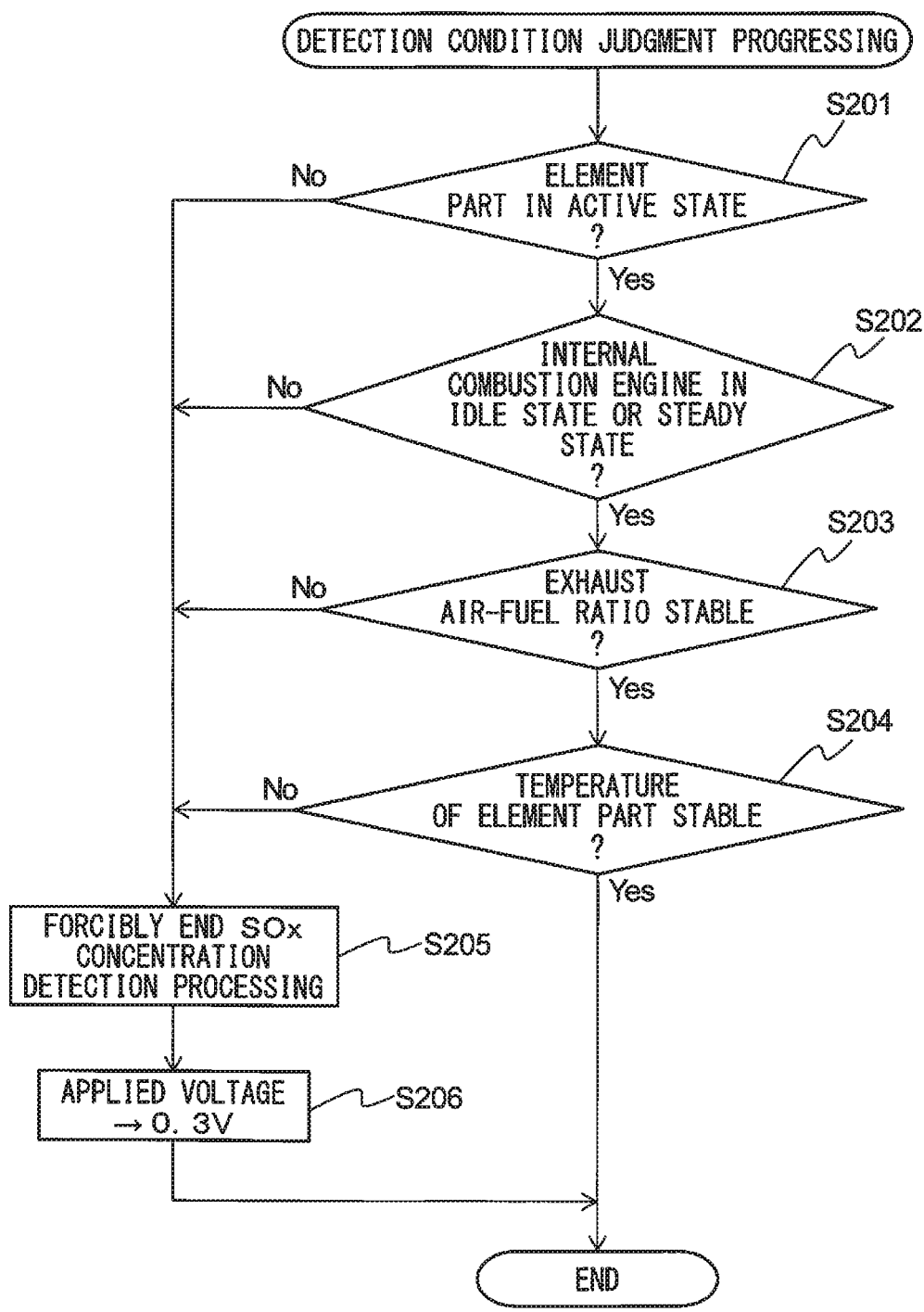
FIG. 12 is a flow chart of a control routine of detection condition judgment processing in the first embodiment of the present invention.

FIG. 12 is a flow chart of a control routine of detection condition judgment processing in the first embodiment of the present invention. The control routine is repeatedly performed at predetermined time intervals by the ECU 80. The control routine judges whether the condition for detection of the $SO_X$ concentration is satisfied. If it judges that the condition for detection of the $SO_X$ concentration is not satisfied, it makes the control routine of the above-mentioned $SO_X$ concentration detection processing forcibly end.

First, at step S201, the estimating part 80a judges whether the element part 10 is in the active state. The estimating part 80a judges that the element part 10 is in the active state if the temperature of the element part 10 is the activation temperature or more. On the other hand, the estimating part 80a judges that the element part 10 is not the active state if the temperature of the element part 10 is less than the activation temperature. The estimating part 80a calculates the temperature of the element part 10 based on the impedance of the element part 10.

If at step S201 it is judged that the element part 10 is not the active state, the control routine proceeds to step S205. In this case, it is impossible to precisely estimate the $SO_X$ concentration in the measured gas using the $SO_X$ detection system 1. For this reason, at step S205, the estimating part 80a makes the control routine of the $SO_X$ concentration detection processing forcibly end. Next, at step S206, the voltage control part 80b sets the voltage applied to the first electrochemical cell to 0.3V. After step S206, the control routine is ended.

On the other hand, if at step S201 the element part 10 is in the active state, the control routine proceeds to step S202. At step S202, the estimating part 80a judges whether the operating state of the internal combustion engine is the idle state or steady state. If at step S202 it is judged that the operating state of the internal combustion engine is not the idle state and steady state, the control routine proceeds to step S205. If the operating state of the internal combustion engine is not the idle state or steady state, the oxygen concentration, water concentration, and $SO_X$ concentration in the measured gas may fluctuate during the detection of the $SO_X$ concentration. For this reason, at step S205, the estimating part 80a makes the control routine of the $SO_X$ concentration detection processing forcibly end.

On the other hand, if at step S202 it is judged that the operating state of the internal combustion engine is the idle state or steady state, the control routine proceeds to step S203. At step S203, the estimating part 80a judges whether the air-fuel ratio of the exhaust gas (measured gas) discharged from the combustion chamber of the internal combustion engine is stable. Note that, the "air-fuel ratio of the exhaust gas (exhaust air-fuel ratio)" means the ratio of the mass of air to the mass of fuel supplied until the exhaust gas is generated (mass of air/mass of fuel) and usually means the ratio of the mass of air to the mass of fuel supplied to the combustion chamber 2 when the exhaust gas is generated.

The judgment at step S203 is, for example, performed by judging whether the amount of change of the exhaust air-fuel ratio is the threshold value or less. If the amount of change of the exhaust air-fuel ratio is the threshold value or less, it is judged that the exhaust air-fuel ratio is stable. On the other hand, if the amount of change of the exhaust air-fuel ratio is larger than the threshold value, it is judged that the exhaust air-fuel ratio is not stable. The exhaust air-fuel ratio is, for example, detected by an air-fuel ratio sensor 104 arranged in the exhaust passage of the internal combustion engine. Further, the threshold value is made a value corresponding to the upper limit value of the amount of change of the exhaust air-fuel ratio enabling the desired detection precision of the $SO_X$ concentration to be obtained. The threshold value is determined in advance by experiments or calculations and is for example ±10%.

If at step S203 it is judged that the exhaust air-fuel ratio is not stable, the control routine proceeds to step S205. If the exhaust air-fuel ratio is not stable, the oxygen concentration, water concentration, and $SO_X$ concentration in the measured gas fluctuate during detection of the $SO_X$ concentration. For this reason, at step S205, the estimating part 80a makes the control routine of the $SO_X$ concentration detection processing forcibly end.

On the other hand, if at step S203 it is judged that the exhaust air-fuel ratio is stable, the control routine proceeds to step S204. At step S204, the estimating part 80a judges whether the temperature of the element part 10 is stable.

The judgment at step S204 is, for example, performed by judging whether the amount of change of the temperature of the element part 10 is a threshold value or less. When the amount of change of the temperature of the element part 10 is the threshold value or less, it is judged that the temperature of the element part 10 is stable. On the other hand, when the amount of change of the temperature of the element part 10 is larger than the threshold value, it is judged that the temperature of the element part 10 is not stable. The estimating part 80a calculates the temperature of the element part 10 based on the impedance of the element part 10. The threshold value is made a value corresponding to the upper limit value of the amount of change of the temperature of the element part 10 enabling the desired precision of detection of the $SO_X$ concentration to be obtained. The threshold value is determined in advance by experiments or calculations and for example is ±50° C.

If at step S204 it is judged that the temperature of the element part 10 is not stable, the control routine proceeds to step S205. If the amount of change of the temperature of the element part 10 at the time of detection of the $SO_X$ concentration is large, the value of the inter-electrode current fluctuates and the $SO_X$ concentration in the measured gas cannot be precisely estimated. For this reason, at step S205, the estimating part 80a makes the control routine of the $SO_X$ concentration detection processing forcibly end.

Therefore, as will be understood from the flow charts of FIG. 11 and FIG. 12, in the present embodiment, the voltage control part 80b performs the first control, poisoning recovery control, and second control while it is judged that the air-fuel ratio of the measured gas and the temperature of the element part 10 are stable. Due to this, it is possible to further improve the precision of detection of the $SO_X$ concentration in the exhaust gas. Further, in the present embodiment, the first control, poisoning recovery control, and second control are consecutively performed. For this reason, there is no wasted time for detection of the $SO_X$ concentration, so the possibility of the air-fuel ratio of the measured gas or the temperature of the element part 10 fluctuating during detection of the $SO_X$ concentration becomes lower.

The configuration and control of the $SO_X$ detection system according to the second embodiment are basically similar to the configuration and control of the $SO_X$ detection system according to the first embodiment except for the points explained below. For this reason, below, the second embodiment of the present invention will be explained focusing on the parts different from the first embodiment.

Figure 13:
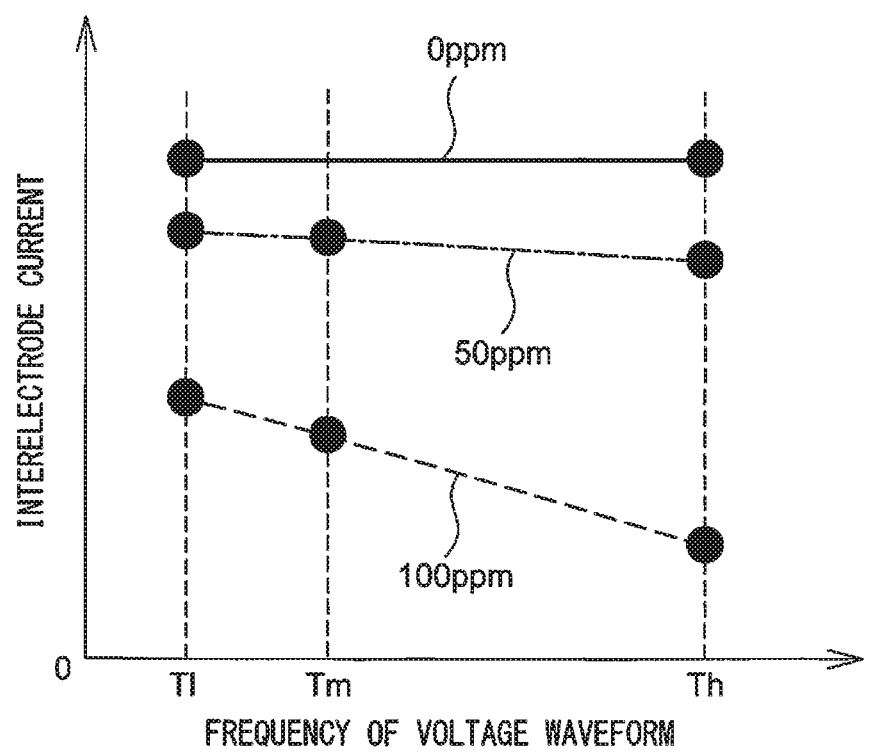
FIG. 13 is a graph showing the relationship between a period of the voltage waveform and inter-electrode current when applying voltage to the first electrochemical cell by a voltage waveform of a sine wave changing between 0.3V and 1.1V.

FIG. 13 is a graph showing the relationship between the period of the voltage waveform and inter-electrode current (maximum value) when applying voltage to the first electrochemical cell 51 by a voltage waveform of a sine wave changing between 0.3V and 1.1V. In the illustrated graph, the maximum values of the inter-electrode current when the period of the voltage waveform (sine wave) is the short period Tl, medium period Tm, and long period Th are plotted. Note that, the longer the period of the voltage waveform, the longer the time during which a voltage of a decomposition start voltage (about 0.6V) or more is applied to the first electrochemical cell 51.

In the illustrated example, three types of measured gases differing in concentrations of $SO_2$ (that is, $SO_X$) contained in the measured gas (0 ppm, 50 ppm, and 100 ppm) were used. In FIG. 13, the solid line, broken line, and one dot chain line respectively show the relationships between the period of the voltage waveform and the inter-electrode current (maximum value) detected at the time of application of voltage in the case of $SO_2$ concentrations in the measured gas of 0 ppm, 100 ppm, and 50 ppm.

To shorten the detection time of $SO_X$ concentration, it is preferable to shorten the period of the voltage waveform of the applied voltage as much as possible. When the $SO_2$ concentration in the measured gas is a relatively high concentration (100 ppm), the difference between the inter-electrode current at the short period Tl and the inter-electrode current in the middle period Tm is a predetermined value or more. In this case, it is possible to quickly estimate the $SO_X$ concentration in the measured gas based on the difference of the inter-electrode currents. However, when the $SO_2$ concentration in the measured gas is a relatively low concentration (50 ppm), the difference between the inter-electrode current at the short period Tl and the inter-electrode current in the middle period Tm is extremely small. In this case, it becomes difficult to estimate the $SO_X$ concentration in the measured gas based on the difference of the inter-electrode currents.

On the other hand, even if the $SO_2$ concentration in the measured gas is a relatively low concentration (50 ppm), the difference between the inter-electrode current at the short period Tl and the inter-electrode current at the long period Th is a predetermined value or more. In this case, the detection time of the $SO_X$ concentration becomes relatively long, but it becomes possible to estimate the $SO_X$ concentration in the measured gas based on the difference of the inter-electrode currents. Therefore, to shorten the detection time of the $SO_X$ concentration while securing the precision of detection of the $SO_X$ concentration, it is necessary to suitably select a combination of periods of voltage waveforms of applied voltage in accordance with the $SO_X$ concentration in the measured gas.

Below, control for detecting the $SO_X$ concentration in the second embodiment will be explained. In the second embodiment, in the same way as the first embodiment, the voltage control part 80b performs first control, poisoning recovery control and second control, and the estimating part 80a estimates the $SO_X$ concentration in the measured gas based on the difference or ratio of the first current detected when the first control is performed and the second current detected when the second control is performed.

The voltage control part 80b performs the third control for making the voltage applied to the first electrochemical cell 51 rise from the first voltage to the second voltage after the second control so that the voltage of the decomposition start voltage or more is applied to the first electrochemical cell 51 for a third period of time if the difference (absolute value) or ratio of the first current and the second current is less than a predetermined value. At this time, the ratio of the first current and the second current is calculated by dividing the first current by the second current when the first period of time is shorter than the second period of time and is calculated by dividing the second current by the first current when the first period of time is longer than the second period of time. The predetermined value is made the lower limit value of a value able to detect the $SO_X$ concentration in the measured gas.

Note that, the voltage control part 80b may perform the third control after the second control when the ratio of the first current and the second current is higher than the predetermined value. At this time, the ratio of the first current and the second current is calculated by dividing the second current by the first current when the first period of time is shorter than the second period of time and is calculated by dividing the first current by the second current when the first period of time is longer than the second period of time. The predetermined value is made the upper limit value of the value enabling detection of the $SO_X$ concentration in the measured gas.

The voltage control part 80b makes the voltage applied to the first electrochemical cell 51 rise from the first voltage to the second voltage by a voltage waveform of a sine wave having a third period in the third control. The third period is a period of 0.1 second to 100 seconds.

The voltage control part 80b performs the fourth control for making the voltage applied to the first electrochemical cell 51 rise from the first voltage to the second voltage after the third control so that the voltage of the decomposition start voltage or more is applied to the first electrochemical cell 51 for a fourth period of time. The fourth period of time is a time different from the third period of time. The voltage control part 80b makes the voltage applied to the first electrochemical cell 51 rise from the first voltage to the second voltage by a voltage waveform of a sine wave having a fourth period in the fourth control. The fourth period is a period of 0.1 second to 100 seconds different from the third period.

Further, the voltage control part 80b performs poisoning recovery control applying voltage enabling desorption of the decomposition products of $SO_X$ adsorbed at the first electrode 41 to the first electrochemical cell 51 between the second control and third control and between the third control and fourth control to desorb the decomposition products of $SO_X$ adsorbed at the first electrode 41 due to the second control or third control.

The voltage control part 80b performs the first control to fourth control so that the sum of the first period of time and the second period of time becomes smaller than the sum of the third period of time and fourth period of time and so that the difference (absolute value) of the third period of time and fourth period of time becomes larger than the difference (absolute value) of the first period of time and second period of time. For this reason, the first period to fourth period are set so that the sum of the first period and second period becomes smaller than the sum of the third period and fourth period and so that the absolute value of the difference between the third period and fourth period becomes larger than the absolute value of the difference between the first period and second period.

For example, the first period and third period are periods of 0.1 to 10 seconds, the second period is a period of 2 to 10 seconds, and the fourth period is a period of 5 to 100 seconds. For example, the first period is set to 1 second, the second period is set to 5 seconds, the third period is set to 1 second, and the fourth period is set to 30 seconds. In this case, the third period of time becomes equal to the first period of time and shorter than the fourth period of time. By performing the third control and fourth control so that the third period of time becomes shorter than the fourth period of time, it is possible to shorten the time of the poisoning recovery control performed between the third period of time and fourth period of time, so it is possible to shorten the time for detection of a low concentration of $SO_X$. Note that, the third period may be set to a period different from the first period, and the third control may be performed so that the third period of time differs from the first period of time.

Note that, in the explanation of the first embodiment, as explained above, the voltage control part 80b may make the voltage applied to the first electrochemical cell 51 rise from the first voltage to the second voltage by a voltage waveform of a square wave having a first time constant in the first control and may make the voltage applied to the first electrochemical cell 51 rise from the first voltage to the second voltage by a voltage waveform of a square wave having a second time constant in the second control. In this case, the voltage control part 80b makes the voltage applied to the first electrochemical cell 51 rise from the first voltage to the second voltage by a voltage waveform of a square wave having a third time constant in the third control and makes the voltage applied to the first electrochemical cell 51 rise from the first voltage to the second voltage by a voltage waveform of a square wave having a fourth time constant in the fourth control.

The third time constant is a time constant of 0.05 second to 50 seconds. Further, the fourth time constant is a time constant of 0.05 second to 50 seconds and is different from the third time constant. The first time constant to fourth time constant is set so that the sum of the first time constant and the second time constant is smaller than the sum of the third time constant and the fourth time constant and so that the absolute value of the difference between the third time constant and the fourth time constant becomes larger than the absolute value of the difference between the first time constant and the second time constant.

The estimating part 80a estimates the $SO_X$ concentration in the measured gas based on the difference between the third current detected by the current detection circuit 62 when the third control is performed and the fourth current detected by the current detection circuit 62 when the fourth control is performed. Specifically, the estimating part 80a estimates that the $SO_X$ concentration in the measured gas is a predetermined low concentration or more when the difference of the third current and fourth current is a predetermined value or more. The predetermined low concentration is a concentration lower than the reference concentration, for example, 50 ppm. The predetermined value is determined in advance by experiments or calculations based on the predetermined low concentration.

For example, the third current is the maximum value of the current detected by the current detection circuit 62 when the third control is performed, while the fourth current is the maximum value of the current detected by the current detection circuit 62 when the fourth control is performed. Note that, the third current may be the current detected when the applied voltage reaches the second voltage by the third control, while the fourth current may be the current detected when the applied voltage reaches the second voltage by the fourth control. Further, the third current may be the cumulative value of the current detected during the third control, while the fourth current may be the cumulative value of the current detected during the fourth control. Further, the third current is the cumulative value of the current detected while a voltage of the decomposition start voltage or more is being applied by the third control, while the fourth current is the cumulative value of the current detected while a voltage of the decomposition start voltage or more is being applied by the fourth control.

Note that, the estimating part 80a may estimate the $SO_X$ concentration in the measured gas based on the ratio of the third current and fourth current. For example, the estimating part 80a estimates that the $SO_X$ concentration in the measured gas is a predetermined low concentration or more if the ratio of the third current and fourth current is a predetermined value or more. At this time, the ratio of the third current and fourth current is calculated by dividing the third current by the fourth current when the third period of time is shorter than the fourth period of time while is calculated by dividing the fourth current by the third current when the third period of time is longer than the fourth period of time. Further, the estimating part 80a may estimate that the $SO_X$ concentration in the measured gas is a predetermined low concentration or more when the ratio of the third current and fourth current is a predetermined value or less. At this time, the ratio of the third current and fourth current is calculated by dividing the fourth current by the third current when the third period of time is shorter than the fourth period of time while is calculated by dividing the third current by the fourth current when the third period of time is longer than the fourth period of time. The predetermined low concentration is a concentration lower than the reference concentration and is for example 50 ppm. The predetermined value is determined in advance by experiments or calculations based on the predetermined low concentration.

Further, the estimating part 80a may estimate the $SO_X$ concentration in the measured gas based on the difference or ratio of other parameters calculated from the third current and fourth current. For example, the estimating part 80a may estimate the $SO_X$ concentration in the measured gas based on the difference or ratio of the resistances between electrodes calculated from the third current and fourth current. The resistances between electrodes are calculated from the third current and fourth current. The difference or ratio of resistances between electrodes is correlated with the difference or ratio of the third current and fourth current, so in this case as well, it can be said that the estimating part 80a estimates the $SO_X$ concentration in the measured gas based on the difference or ratio of the third current and fourth current.

In the present embodiment, it is possible to quickly detect a high concentration of $SO_X$ by the first control and second control and possible to detect a low concentration of $SO_X$ by the third control and fourth control.

Figure 14:
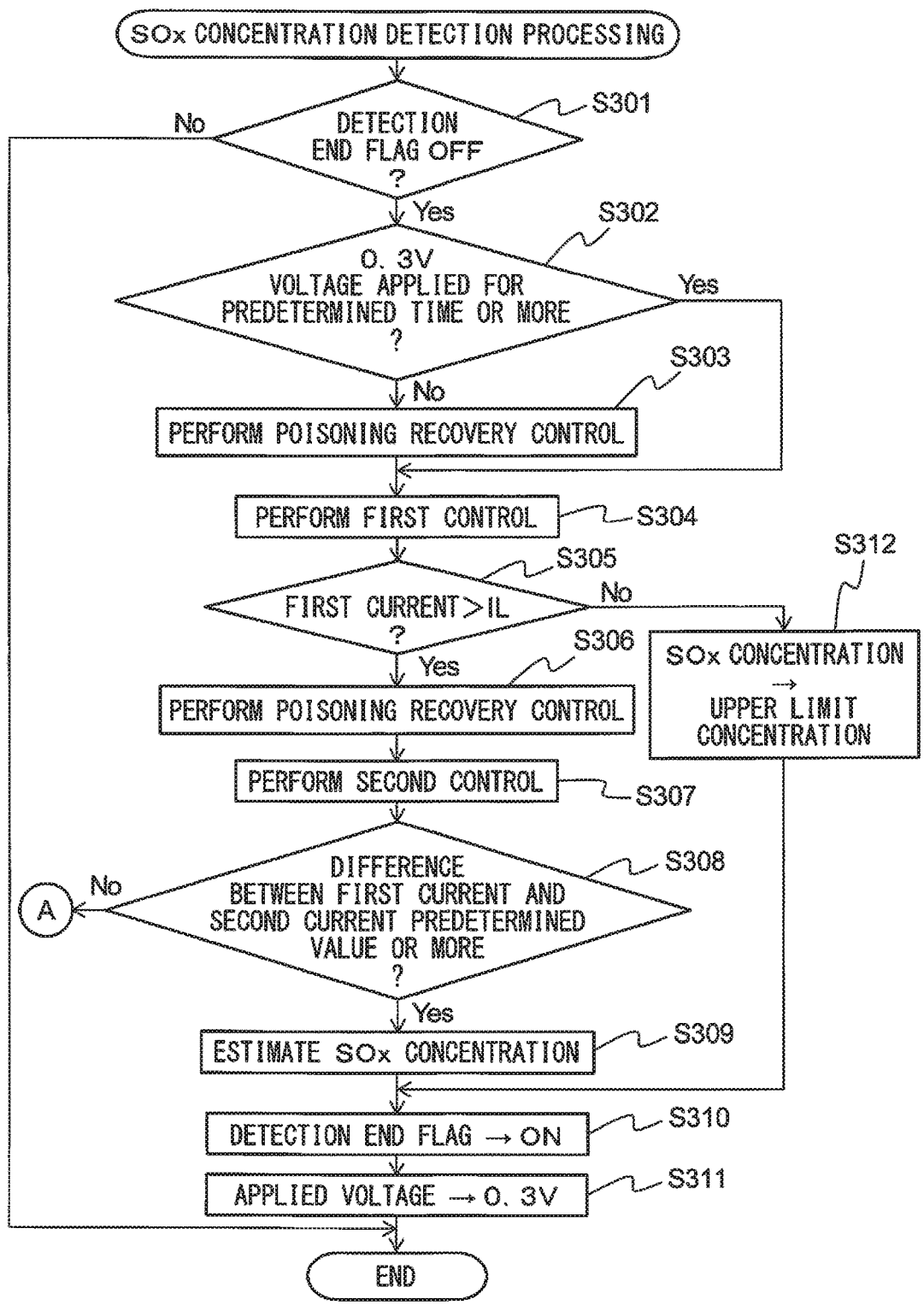
FIG. 14 is a flow chart of a control routine of $SO_X$ concentration detection processing in the second embodiment of the present invention.
Figure 15:
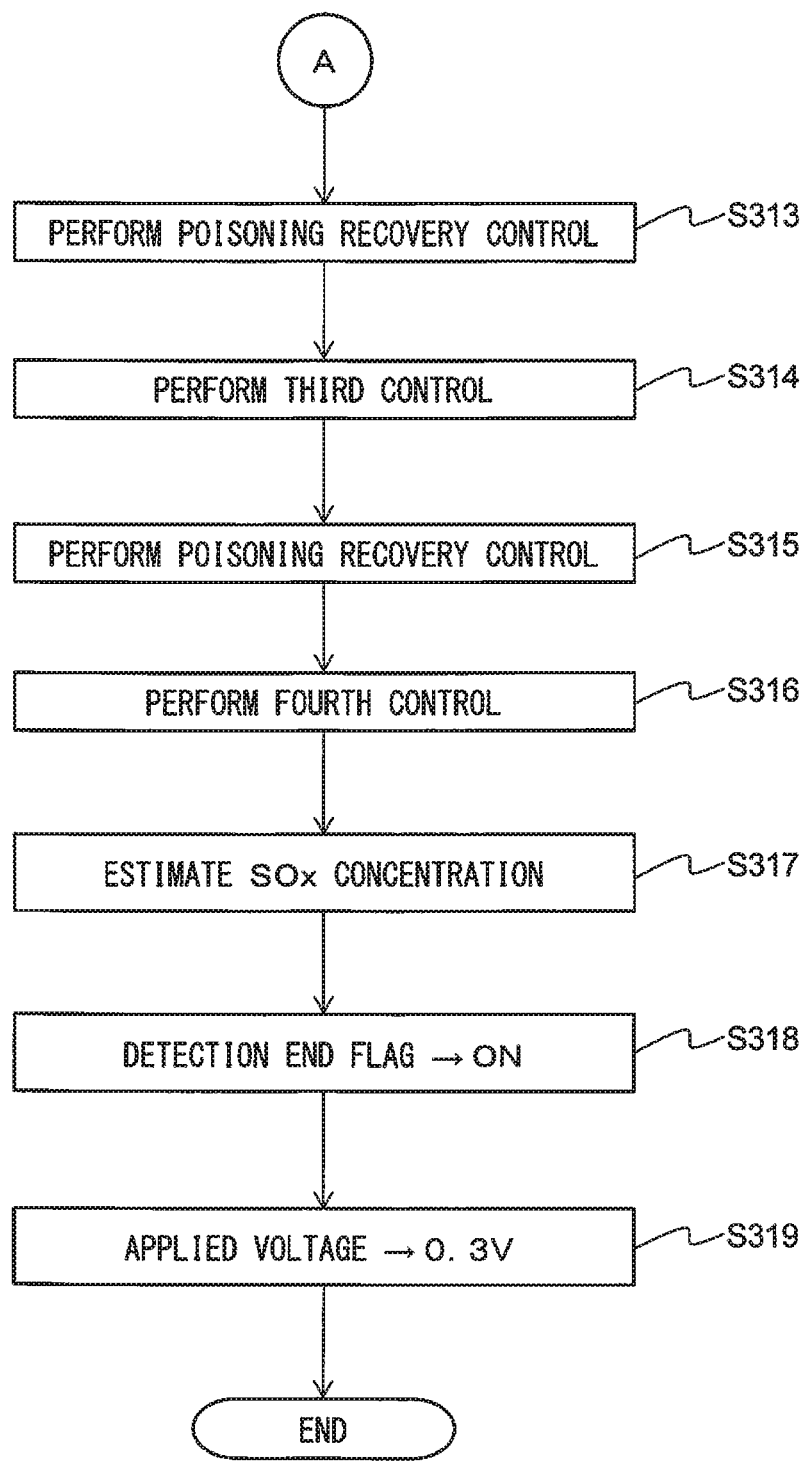
FIG. 15 is a flow chart of a control routine of $SO_X$ concentration detection processing in the second embodiment of the present invention.

Below, referring to the flow chart of FIG. 14 and FIG. 15, the $SO_X$ concentration detection processing in the second embodiment will be explained. FIG. 14 and FIG. 15 are flow charts of a control routine of $SO_X$ concentration detection processing in the second embodiment of the present invention. The control routine is repeatedly performed by the ECU 80. Further, the control routine is made to forcibly end even if in progress when it is judged in the detection condition judgment processing shown in FIG. 12 that a condition for detection of the $SO_X$ concentration is not satisfied. Step S301 to step S307 and step S309 to step S312 in FIG. 14 are similar to step S101 to step S107 and step S108 to step S111 in FIG. 11, so explanations will be omitted.

The control routine proceeds to step S308 after step S307. At step S308, the estimating part 80a judges whether the difference of the first current detected when first control is performed and the second current when second control is performed is a predetermined value or more. The predetermined value is made the lower limit value of the values enabling detection of the $SO_X$ concentration in the measured gas. If at step S308 it is judged that the difference of the first current and the second current is a predetermined value or more, the control routine proceeds to step S309. On the other hand, if at step S308 it is judged that the difference of the first current and the second current is less than a predetermined value, the control routine proceeds to step S313.

At step S313, the voltage control part 80b performs poisoning recovery control to desorb the decomposition products of $SO_X$ adsorbed at the first electrode 41 due to the second control. Specifically, the voltage control part 80b applies a voltage able to desorb decomposition products of $SO_X$ adsorbed at the first electrode 41 to the first electrochemical cell 51 for a predetermined time. The applied voltage to the first electrochemical cell 51 is for example 0.3V. The predetermined time is made a time sufficient for desorption of the decomposition products of $SO_X$ adsorbed at the first electrode 41 by the second control.

Next, at step S314, the voltage control part 80b performs third control. Specifically, the voltage control part 80b makes the voltage applied to the first electrochemical cell 51 rise from the first voltage to the second voltage so that the voltage of the decomposition start voltage or more is applied to the first electrochemical cell 51 for the third period of time. Further, the voltage control part 80b makes the voltage applied to the first electrochemical cell 51 rise from the first voltage to the second voltage by a voltage waveform of a sine wave having a third period at the third control. The third period is 0.1 second to 100 seconds. For example, the third period is 1 second which is the same period as the first period. The current detection circuit 62 detects the inter-electrode current while the third control is being performed.

At step S315, the voltage control part 80b performs poisoning recovery control to desorb the decomposition products of $SO_X$ adsorbed at the first electrode 41 due to the third control. Specifically, the voltage control part 80b applies a voltage enabling the decomposition products of $SO_X$ adsorbed at the first electrode 41 to be desorbed to the first electrochemical cell 51 for a predetermined time. The voltage applied to the first electrochemical cell 51 is for example 0.3V. The predetermined time is made a sufficient time for desorption of the decomposition products of $SO_X$ adsorbed at the first electrode 41 due to the third control.

Next, at step S316, the voltage control part 80b performs fourth control. Specifically, the voltage control part 80b makes the voltage applied to the first electrochemical cell 51 rise from the first voltage to the second voltage so that the voltage of the decomposition start voltage or more is applied to the first electrochemical cell 51 for the fourth period of time. Further, the voltage control part 80b makes the voltage applied to the first electrochemical cell 51 rise from the first voltage to the second voltage by a voltage waveform of a sine wave having a fourth period at the fourth control. The fourth period is a period of 0.1 second to 100 seconds different from the third period. For example, the fourth period is a period longer than the second period and third period, that is, 30 seconds. The current detection circuit 62 detects the inter-electrode current while the fourth control is being performed.

Next, at step S317, the estimating part 80a estimates the $SO_X$ concentration in the measured gas based on the difference of the third current detected by the current detection circuit 62 when the third control is performed and the fourth current detected by the current detection circuit 62 when the fourth control is performed. The third current is the maximum value of current detected by the current detection circuit 62 when the third control is performed. The fourth current is the maximum value of current detected by the current detection circuit 62 when the fourth control is performed. Specifically, the estimating part 80a estimates that the $SO_X$ concentration in the measured gas is a predetermined low concentration or more when the difference of the third current and fourth current is a predetermined value or more. The predetermined low concentration is a concentration lower than the reference concentration, for example, 50 ppm. The predetermined value is determined in advance by experiments or calculations based on the predetermined low concentration.

Next, at step S318, since the $SO_X$ concentration finishes being detected at step S317, the detection completion flag is set on. Next, at step S319, the decomposition products of $SO_X$ adsorbed at the first electrode 41 due to the fourth control are desorbed by the voltage control part 80b setting the voltage applied to the first electrochemical cell to 0.3V. After step S319, the control routine is ended.

Note that, the fourth period may be made shorter than the third period so that the fourth period of time becomes shorter than the third period of time. Further, the voltage control part 80b may make the voltage applied to the first electrochemical cell 51 rise from the first voltage to the second voltage by a voltage waveform of a square wave having a third time constant in the third control of step S314 and make the voltage applied to the first electrochemical cell 51 rise from the first voltage to the second voltage by a voltage waveform of a square wave having a fourth time constant in the fourth control of step S316. The third time constant is a time constant of 0.05 second to 50 seconds, for example, 0.5 second. Further, the fourth time constant is a time constant of 0.05 second to 50 seconds and is different from the third time constant, for example, 15 seconds.

Further, the third current may be the current detected when the applied voltage reaches the second voltage by the third control while the fourth current may be the current detected when the applied voltage reaches the second voltage by the fourth control. Further, the third current may be the cumulative value of the current detected during the third control while the fourth current may be the cumulative value of the current detected during the fourth control. Further, the third current may be the cumulative value of the current detected while voltage of the decomposition start voltage or more is applied by the third control while the fourth current may be the cumulative value of the current detected while voltage of the decomposition start voltage or more is applied by the fourth control.

Further, at step S317, the estimating part 80a may estimate the $SO_X$ concentration in the measured gas based on the ratio of the third current and the fourth current. Further, the third control at step S314 and the fourth control at step S316 may respectively be performed a plurality of times. In this case, the third current and fourth current are respectively made average values of current values detected a plurality of times.

The configuration and control of the $SO_X$ detection system according to the third embodiment are basically similar to the configurations and controls of the first embodiment and the second embodiment except for the points explained below. For this reason, below, the third embodiment of the present invention will be explained focusing on the parts different from the first embodiment and the second embodiment.

Figure 16:
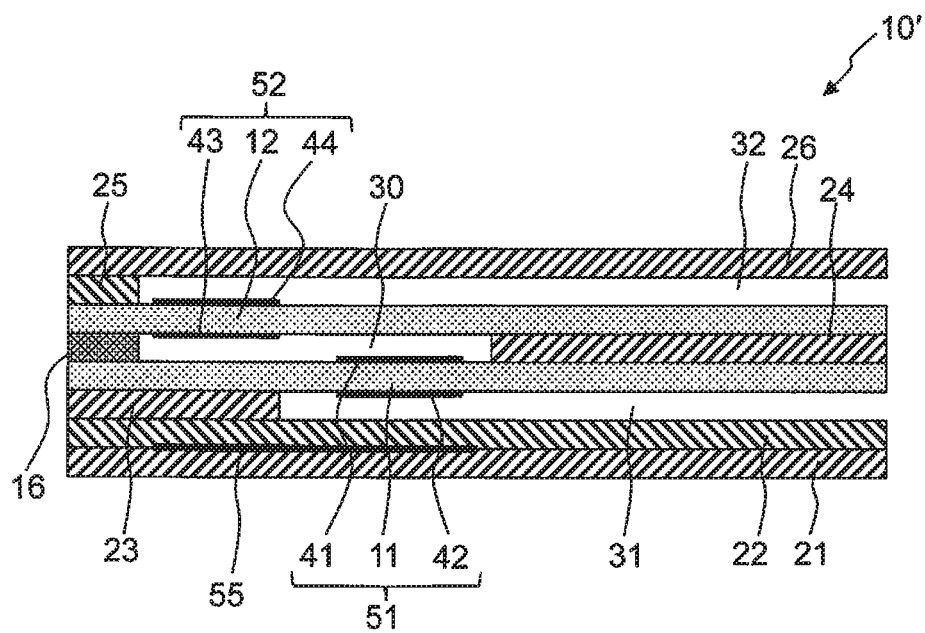
FIG. 16 is a schematic cross-sectional view showing the configuration of an element part of a $SO_X$ detection system according to a third embodiment of the present invention.

FIG. 16 is a schematic cross-sectional view showing the configuration of an element part 10' of the $SO_X$ detection system according to the third embodiment of the present invention. The $SO_X$ detection system according to the third embodiment comprises the element part 10'. The element part 10' is configured similar to the element parts 10 in the first embodiment and the second embodiment except for the point of provision of the second electrochemical cell 52 in addition to the first electrochemical cell 51.

As shown in FIG. 16, the element part 10' is comprised of a plurality of layers stacked together. Specifically, the element part 10' comprises a first solid electrolyte layer 11, a second solid electrolyte layer 12, a diffusion regulating layer 16, a first barrier layer 21, a second barrier layer 22, a third barrier layer 23, a fourth barrier layer 24, a fifth barrier layer 25, and a sixth barrier layer 26.

The second solid electrolyte layer 12 has a configuration similar to the first solid electrolyte layer 11. The sixth barrier layer 26 has a configuration similar to the first barrier layer 21 to the fifth barrier layer 25. The layers of the element part 10', from the bottom in FIG. 16, are comprised of the first barrier layer 21, second barrier layer 22, third barrier layer 23, first solid electrolyte layer 11, diffusion regulating layer 16 and fourth barrier layer 24, second solid electrolyte layer 12, fifth barrier layer 25, and sixth barrier layer 26 stacked in that order.

The first solid electrolyte layer 11, second solid electrolyte layer 12, diffusion regulating layer 16, and fourth barrier layer 24 define and form the measured gas chamber 30. Note that, the measured gas chamber 30 may be configured in any way so long as configured so as to adjoin the first solid electrolyte layer 11 and the second solid electrolyte layer 12 and have measured gas flow into it.

The second solid electrolyte layer 12, fifth barrier layer 25, and sixth barrier layer 26 define and form a second atmospheric chamber 32. As will be understood from FIG. 16, the second atmospheric chamber 32 is arranged at an opposite side to the measured gas chamber 30 across the second solid electrolyte layer 12. The second atmospheric chamber 32 is opened to the atmosphere at the outside of the exhaust passage. Therefore, atmospheric gas flows into the second atmospheric chamber 32 as well. Note that, the second atmospheric chamber 32 may be configured in any way so long as configured so as to adjoin the second solid electrolyte layer 12 and have atmosphere flow into it.

The element part 10' further comprises a third electrode 43 and a fourth electrode 44. The third electrode 43 is arranged on the surface of the second solid electrolyte layer 12 at the measured gas chamber 30 side. Therefore, the third electrode 43 is exposed to the measured gas inside the measured gas chamber 30. Further, the third electrode 43 is arranged inside the measured gas chamber 30 at the diffusion regulating layer 16 side from the first electrode 41. Therefore, the measured gas flowing through the diffusion regulating layer 16 into the inside of the measured gas chamber 30 first flows around the third electrode 43, then flows around the first electrode 41. On the other hand, the fourth electrode 44 is arranged on the surface of the second solid electrolyte layer 12 at the second atmospheric chamber 32 side. Therefore, the fourth electrode 44 is exposed to the gas (atmosphere) in the second atmospheric chamber 32. The third electrode 43 and the fourth electrode 44 are arranged to face each other across the second solid electrolyte layer 12. The third electrode 43, second solid electrolyte layer 12, and fourth electrode 44 form the second electrochemical cell 52.

The third electrode 43 and the fourth electrode 44 are porous cermet electrodes including platinum (Pt) as main components. However, the material forming the third electrode 43 is not necessarily limited to the above material. It may be any material so long as one able to reduce and decompose the oxygen contained in the measured gas in the measured gas chamber 30 when applying a predetermined voltage between the third electrode 43 and the fourth electrode 44. Further, the material forming the fourth electrode 44 is also not necessarily limited to the above material. It may be any material so long as oxide ions can be made to move between the third electrode 43 and the fourth electrode 44 when applying a predetermined voltage between the third electrode 43 and the fourth electrode 44.

The third electrode 43 and the fourth electrode 44 are connected to the voltage application circuit 61. The voltage application circuit 61 applies voltage to the second electrochemical cell 52 so that the potential of the fourth electrode 44 becomes higher than the potential of the third electrode 43. The voltage applied to the second electrochemical cell 52 is controlled by the voltage control part 80b of the ECU 80.

The current detection circuit 62 detects the inter-electrode current flowing between the third electrode 43 and the fourth electrode 44 (that is, the current flowing through the second solid electrolyte layer 12). The output of the current detection circuit 62 is input through the AD converter 87 to the estimating part 80a of the ECU 80. Therefore, the estimating part 80a can acquire the inter-electrode current of the second electrochemical cell 52 from the current detection circuit 62.

Figure 17:
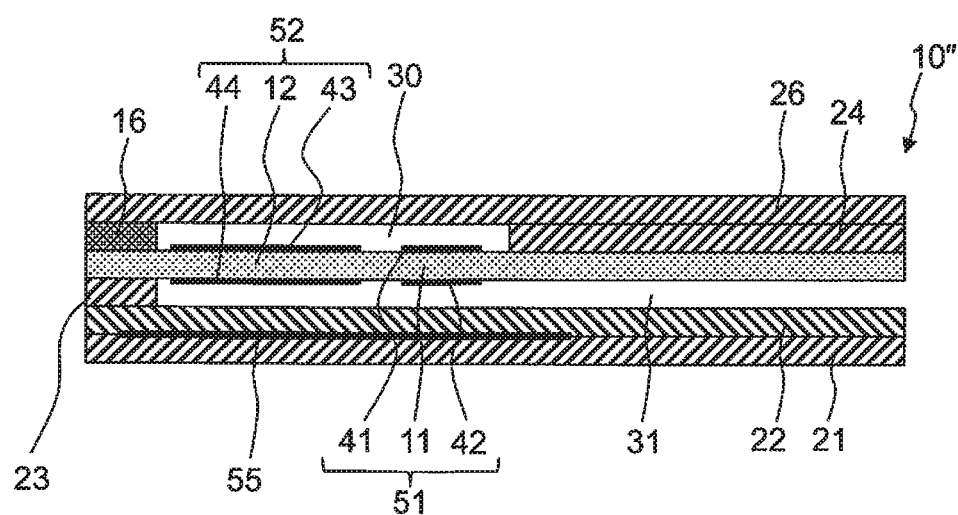
FIG. 17 is a schematic cross-sectional view showing another configuration of an element part of the $SO_X$ detection system according to the third embodiment of the present invention.

Note that, in the element part 10' shown in FIG. 16, the second solid electrolyte layer 12 forming the second electrochemical cell 52 is a separate solid electrolyte layer from the first solid electrolyte layer 11 forming the first electrochemical cell 51. However, like in the element part 10" shown in FIG. 17, the first solid electrolyte layer 11 and the second solid electrolyte layer 12 may be a single solid electrolyte layer. In this case, there is a single atmospheric chamber of the element part. The first electrode 41 is arranged at the surface of the first solid electrolyte layer 11 at the measured gas chamber 30 side, while the second electrode 42 is arranged at the surface of the first solid electrolyte layer 11 at the atmospheric chamber 31 side. Further, the third electrode 43 is arranged on the surface of the second solid electrolyte layer 12 at the measured gas chamber 30 side, while the fourth electrode 44 is arranged on the surface of the second solid electrolyte layer 12 at the atmospheric chamber 31 side.

In the first electrochemical cell 51, as explained above, a predetermined voltage of the decomposition start voltage of $SO_X$ and water or more is applied between the first electrode 41 and the second electrode 42 to make the water and $SO_X$ decompose on the first electrode 41 and the inter-electrode current accompanying the decomposition of water is detected. However, if the measured gas reaching the first electrochemical cell 51 contains oxygen, oxygen decomposes (ionization occurs) on the first electrode 41 and the oxide ions formed due to this flow from the first electrode 41 to the second electrode 42. For this reason, to precisely detect the decomposition current of water at the first electrochemical cell 51, it is preferable to remove the oxygen in the measured gas before the measured gas reaches the first electrochemical cell 51.

Here, if applying voltage within the limit current region of oxygen to the second electrochemical cell 52, the speed of conduction of oxide ions able to be conducted by the second electrochemical cell 52 becomes faster than the speed of introduction of oxygen introduced through the diffusion regulating layer 16 to the measured gas chamber 30. Therefore, if the voltage within the limit current region of oxygen is applied to the second electrochemical cell 52, almost all of the oxygen contained in the measured gas flowing through the diffusion regulating layer 16 into the measured gas chamber 30 can be removed.

Therefore, in the third embodiment, when using the first electrochemical cell 51 to detect the $SO_X$ concentration in the measured gas, a voltage in the limit current region of oxygen is applied to the second electrochemical cell 52 arranged at the diffusion regulating layer 16 side from the first electrochemical cell 51. The limit current region of oxygen is the region of the lower limit voltage (for example, 0.1V) where even if making the applied voltage rise further, the inter-electrode current does not change much at all or more. Further, the voltage applied to the second electrochemical cell 52 is made a voltage less than the decomposition start voltage of the water and $SO_X$ (about 0.6V). Due to this, it is possible to decompose and remove oxygen in the second electrochemical cell 52 without decomposing the water and $SO_X$. Therefore, the second electrochemical cell 52 functions as a pump cell discharging oxygen without discharging water and $SO_X$ from inside the measured gas chamber 30. Due to this, the oxygen in the measured gas is removed at the second electrochemical cell 52 before the measured gas reaches the first electrochemical cell 51, so it is possible to further improve the detection precision of the $SO_X$ concentration of the first electrochemical cell 51.

Further, as explained above, by applying a voltage of the lower limit voltage of the limit current region of oxygen or more to the second electrochemical cell 52, the oxygen contained in the measured gas is decomposed at the third electrode 43 and the oxide ions produced by this decomposition are exhausted from the measured gas chamber 30 to the second atmospheric chamber 32. At this time, by detecting the inter-electrode current flowing between the third electrode 43 and the fourth electrode 44 by the current detection circuit 62, it is possible to detect the oxygen concentration in the measured gas. Therefore, the second electrochemical cell 52 may be used as an air-fuel ratio sensor for detecting an exhaust air-fuel ratio. In this case, at step S203 of FIG. 12, the exhaust air-fuel ratio is detected by the second electrochemical cell 52.

In the third embodiment, the voltage control part 80b of the ECU 80 applies a voltage of the lower limit voltage of the limit current region of oxygen or more and of less than the decomposition start voltage of the water and $SO_X$ to the second electrochemical cell 52. For example, the voltage control part 80b applies a voltage of 0.1V to less than 0.6V, for example, a voltage of 0.4V to the second electrochemical cell 52 when the temperature of the element part 10' reaches the activation temperature. After that, the voltage control part 80b maintains the voltage applied to the second electrochemical cell 52 at 0.4V.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations

REFERENCE SIGNS LIST

1. $SO_X$ detection system
10, 10', 10". element part
11. first solid electrolyte layer
16. diffusion regulating layer
41. first electrode
42. second electrode
51. first electrochemical cell
61. voltage application circuit
62. current detection circuit
80. electronic control unit (ECU)

80a. estimating part
80b. voltage control part

The invention claimed is:

1. A sulfur oxide detection system comprising;
an element part which includes a sensor cell having a solid electrolyte layer having oxide ion conductivity, a first electrode arranged on one side surface of the solid electrolyte layer so as to be exposed to a measured gas, and a second electrode arranged at the other side surface of the solid electrolyte layer to be exposed to an atmosphere and includes a diffusion regulating layer regulating diffusion of the measured gas and which is arranged in an exhaust passage of an internal combustion engine;
a voltage application circuit configured to apply a voltage to the sensor cell so that a potential of the second electrode becomes higher than a potential of the first electrode;
a current detection circuit configured to detect a current flowing between the first electrode and the second electrode; and
a controller communicatively coupled with the voltage application circuit and the current detection circuit, wherein the controller is configured to:
perform first control making the voltage applied to the sensor cell rise from a first voltage less than a decomposition start voltage of water and sulfur oxide to a second voltage higher than the decomposition start voltage so that a voltage of the decomposition start voltage or more is applied to the sensor cell for a first period of time, after the first control, perform second control making the voltage applied to the sensor cell rise from the first voltage to the second voltage so that the voltage of the decomposition start voltage or more is applied to the sensor cell for a second period of time different from the first period of time, and, between the first control and the second control, perform poisoning recovery control applying a voltage enabling desorption of decomposition products of sulfur oxide adsorbed at the first electrode to the sensor cell; and
to estimate a sulfur oxide concentration in the measured gas based on a difference or a ratio of a first current detected by the current detection circuit when the first control is performed and a second current detected by the current detection circuit when the second control is performed.

2. The sulfur oxide detection system according to claim 1, wherein
the controller is configured to make the voltage applied to the sensor cell rise from the first voltage to the second voltage by a voltage waveform of a sine wave having a first period of 0.1 second to 100 seconds in the first control, and make the voltage applied to the sensor cell rise from the first voltage to the second voltage by a voltage waveform of a sine wave having a second period of 0.1 second to 100 seconds different from the first period in the second control.

3. The sulfur oxide detection system according to claim 1, wherein the controller is configured to make the voltage applied to the sensor cell rise from the first voltage to the second voltage by a voltage waveform of a square wave having a first time constant of 0.05 second to 50 seconds in the first control, and make the voltage applied to the sensor cell rise from the first voltage to the second voltage by a voltage waveform of a square wave having a second time constant of 0.05 second to 50 seconds different from the first time constant in the second control.

4. The sulfur oxide detection system according to claim 1, wherein the controller is configured to estimate the sulfur oxide concentration in the measured gas based on the difference of the first current and the second current, and estimate that the sulfur oxide concentration in the measured gas is a reference concentration or more when the difference is a reference value or more.

5. The sulfur oxide detection system according to claim 1, wherein
the controller is configured to estimate the sulfur oxide concentration in the measured gas based on the ratio of the first current and the second current, and estimate that the sulfur oxide concentration in the measured gas is a reference concentration or more when the ratio is a reference value or more, and
the controller is configured to calculate the ratio by dividing the first current by the second current if the first period of time is shorter than the second period of time and by dividing the second current by the first current if the first period of time is longer than the second period of time.

6. The sulfur oxide detection system according to claim 1, wherein
the controller is configured to estimate the sulfur oxide concentration in the measured gas based on the ratio of the first current and the second current, and estimate that the sulfur oxide concentration in the measured gas is a reference concentration or more if the ratio is a reference value or less, and
the controller is configured to calculate the ratio by dividing the second current by the first current if the first period of time is shorter than the second period of time and by dividing the first current by the second current if the first period of time is longer than the second period of time.

7. The sulfur oxide detection system according to claim 1, wherein the first period of time is shorter than the second period of time.

8. The sulfur oxide detection system according to claim 1, wherein the controller is configured to estimate that the sulfur oxide concentration in the measured gas is an upper limit concentration or more if the first current is a lower limit value or less.

9. The sulfur oxide detection system according to claim 1, wherein the controller is configured to estimate that the sulfur oxide concentration in the measured gas is an upper limit concentration or more if the first current is a first lower limit value or less and the second current is a second lower limit value or less.

10. The sulfur oxide detection system according to claim 1, wherein
the controller is configured to judge whether an air-fuel ratio of the measured gas and a temperature of the element part are stable, and
the controller is configured to perform the first control, the poisoning recovery control, and the second control while it is judged that the air-fuel ratio of the measured gas and the temperature of the element part are stable.

11. The sulfur oxide detection system according to claim 1, wherein the first current is a maximum value of current detected by the current detection circuit when the first control is performed and the second current is a maximum value of current detected by the current detection circuit when the second control is performed.

12. The sulfur oxide detection system according to claim 1, wherein if the difference or the ratio of the first current and the second current is less than a predetermined value, the controller is configured to perform third control making the voltage applied to the sensor cell rise from the first voltage to the second voltage after the second control so that the voltage of the decomposition start voltage or more is applied to the sensor cell for a third period of time, perform fourth control making the voltage applied to the sensor cell rise from the first voltage to the second voltage after the third control so that the voltage of the decomposition start voltage or more is applied to the sensor cell for a fourth period of time, and perform the poisoning recovery control between the second control and the third control and between the third control and the fourth control, and a sum of the first period of time and the second period of time is smaller than a sum of the third period of time and the fourth period of time and a difference of the third period of time and the fourth period of time is larger than a difference of the first period of time and the second period of time, the controller is configured to calculate the ratio by dividing the first current by the second current if the first period of time is shorter than the second period of time and by dividing the second current by the first current if the first period of time is longer than the second period of time, and the controller is configured to estimate the sulfur oxide concentration in the measured gas based on a difference or a ratio of the third current detected by the current detection circuit when the third control is performed and the fourth current detected by the current detection circuit when the fourth control is performed.

13. The sulfur oxide detection system according to claim 12, wherein the third period of time is shorter than the fourth period of time.

14. The sulfur oxide detection system according to claim 1, wherein if the ratio of the first current and the second current is higher than a predetermined value, the controller is configured to perform third control making the voltage applied to the sensor cell rise from the first voltage to the second voltage after the second control so that the voltage of the decomposition start voltage or more is applied to the sensor cell for a third period of time, perform fourth control making the voltage applied to the sensor cell rise from the first voltage to the second voltage after the third control so that the voltage of the decomposition start voltage or more is applied to the sensor cell for a fourth period of time, and perform the poisoning recovery control between the second control and the third control and between the third control and the fourth control, and a sum of the first period of time and the second period of time is smaller than a sum of the third period of time and the fourth period of time and a difference of the third period of time and the fourth period of time is larger than a difference of the first period of time and the second period of time, the controller is configured to calculate the ratio by dividing the second current by the first current if the first period of time is shorter than the second period of time and by dividing the first current by the second current if the first period of time is longer than the second period of time, and the controller is configured to estimate the sulfur oxide concentration in the measured gas based on a difference or a ratio of the third current detected by the current detection circuit when the third control is performed and the fourth current detected by the current detection circuit when the fourth control is performed.

15. The sulfur oxide detection system according to claim 14, wherein the third period of time is shorter than the fourth period of time.

* * * * *